US010342818B2

(12) United States Patent
Lin et al.

(10) Patent No.: US 10,342,818 B2
(45) Date of Patent: Jul. 9, 2019

(54) DUAL-ACTION COMPOUNDS TARGETING ADENOSINE A$_{2A}$ RECEPTOR AND ADENOSINE TRANSPORTER FOR PREVENTION AND TREATMENT OF NEURODEGENERATIVE DISEASES

(71) Applicant: Academia Sinica, Taipei (TW)

(72) Inventors: Yun-Lian Lin, Taipei (TW); Yijuang Chern, Taipei (TW); Jim-Min Fang, Taipei (TW); Jung-Hsing Lin, Taipei (TW); Nai-Kuei Huang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 359 days.

(21) Appl. No.: 14/849,782

(22) Filed: Sep. 10, 2015

(65) Prior Publication Data

US 2015/0374737 A1 Dec. 31, 2015

Related U.S. Application Data

(62) Division of application No. 13/508,797, filed as application No. PCT/US2010/056516 on Nov. 12, 2010, now abandoned.

(60) Provisional application No. 61/260,932, filed on Nov. 13, 2009.

(51) Int. Cl.
| | | |
|---|---|---|
| *A01N 43/04* | (2006.01) | |
| *A61K 31/70* | (2006.01) | |
| *A61K 31/7076* | (2006.01) | |
| *C07H 19/167* | (2006.01) | |
| *A61K 31/706* | (2006.01) | |
| *A61K 31/7064* | (2006.01) | |

(52) U.S. Cl.
CPC ....... *A61K 31/7076* (2013.01); *C07H 19/167* (2013.01); *A61K 31/706* (2013.01); *A61K 31/7064* (2013.01)

(58) Field of Classification Search
None
See application file for complete search history.

(56) References Cited

U.S. PATENT DOCUMENTS

| | | | | |
|---|---|---|---|---|
| 3,590,029 A * | 6/1971 | Koch et al. | ................ | 260/211.5 |
| 2003/0225205 A1 | 12/2003 | Epple | | |
| 2007/0237840 A1 | 10/2007 | Chern et al. | | |
| 2007/0249638 A1 | 10/2007 | Giorgio et al. | | |
| 2008/0064653 A1 | 3/2008 | Li | | |
| 2008/0132525 A1 | 6/2008 | Wahhab et al. | | |
| 2008/0176816 A1 | 7/2008 | Chem et al. | | |

FOREIGN PATENT DOCUMENTS

WO WO 2008/156513 A2 12/2008

OTHER PUBLICATIONS

Huang et al. J. Nat. Prod. (2007), vol. 70, pp. 571-574.*
Ross et al. The Lancet (2011), vol. 10, pp. 83-98.*
Tansey et al. Neurobiology of Disease (2010), vol. 37, pp. 510-518.*
Cummings et al. Alzheimer's Research & Therapy (2014), pp. 1-7.*
Afify, H. M. N. M. et al., "A Novel and Facile Reaction to N6-Alkylated Adenosine via Benzotriazole as a Synthetic Auxiliary", Journal of Heterocyclic Chemistry, Wiley-Blackwell Publishing, Mar. 1, 2000, vol. 37, No. 2, pp. 339-341.
Aronov et al., "Synthesis and Structure-Activity Relationships of Adenosine Analogs as Inhibitors of Trypanosomal Glyceraldehyde-3-Phosphate Dehydrogenase. Modifications at Positions 5' and 8'", Bio. & Med. Chem. Let., Pergamon Elsevier Sci., Dec. 15, 1998, vol. 8, No. 24, pp. 3505-3510.
Bressi J. C. et al., "Adenosine Analogues as Inhibitors of Trypanosoma brucei Phosphoglycerate Kinase: Elucidation of a Novel Binding Mode for a 2-Amino-N6-Substituted Adenosine", J. of Medical Chemistry, American Chemical Society, Jan. 1, 2000, vol. 43, No. 22, pp. 4135-4150.
Claudia Herforth et al., "Polymer-bound reagents for the introduction of spacer-modified biotin labels", Bioorganic & Medical Chemistry, Jun. 1, 2004, vol. 12, No. 11, pp. 2895-2902.
De Sarro G. et al., "Effects of adenosine receptor agonists and antagonists on audiogenic seizure-sensible DBA/2 mice", European Journal of Pharmacology, Elsevier Science, Apr. 9, 1999, vol. 371, pp. 137-145.
Dolezal et al., "Preparation, biological activity and endogenous occurrence of N6-benzyladenosines", Bioorganic & Medical Chemistry, Pergamon, Apr. 26, 2007, vol. 15, No. 11, pp. 3737-3747.
Gallo-Rodriguez C. et al., "Structure Activity Relationships of N6-Benzyladenosine-5'-uronamides as A3-Selective Adenosine Agonists", Journal of Medical Chemistry, American Chemical Society, Mar. 4, 1994, vol. 37, No. 5, pp. 636-646.
Golisade A. et al., "Anti-Malarial Activity of N6-Substituted Adenosine Derivatives Part I", Jan. 1, 2002, vol. 10, pp. 769-777.
Kusachi S. et al., "Dog Coronary Artery Adenosine Receptor: Structure of the N6-Aryl Subregion", J, of Med. Chem., American Chemical Society, 1986, vol. 29, pp. 989-996.
Lauren P. Shearman et al., "[125I]4-Aminobenzyl-5'-N-methylcarboxamidoadenosine ([125I]AB-MECA) labels multiple adenosine receptor subtypes in rat brain", Brain Research, Jan. 1, 1997, vol. 745, No. 1-2, pp. 10-20.
Mauborgne, Annie et al., "Adenosine receptor-mediated control of in vitro release of pain-related neuropeptides from the rat spinal cord", European Journal of Pharmacology, 2002, vol. 441, No. 1-2, pp. 47-55.

(Continued)

*Primary Examiner* — Patrick T Lewis
(74) *Attorney, Agent, or Firm* — Birch, Stewart, Kolasch & Birch, LLP

(57) ABSTRACT

The present invention provides therapeutic agents for preventing and treating neurodegenerative diseases. These agents synergistically target both the adenosine A$_{2A}$ receptor (A$_{2A}$R) and the equilibrative nucleoside transporter 1 (ENT1).

4 Claims, 9 Drawing Sheets

(56) References Cited

OTHER PUBLICATIONS

Qing Lin et al., "Design of Allele-Specific Protein Methyltransferase Inhibitors", Journal of American Chemical Society, Nov. 1, 2001, vol. 123, No. 47, pp. 11608-11613.
Sheardown, Malcolm, J. et al., "Unexpected Neuroprotection Observed With the Adenosine A2A Receptor Agonist CGS 21680", Drug Development Research, 1996, vol. 39, No. 1, pp. 108-114.
Ueeda M. et al., "2-Alkoxyadenosines: Potent and Selective Agonists at the Coronary Artery A2 Adenosine Receptor", Journal of Medical Chemistry, American Chemical Society, Jan. 1, 1991, vol. 34, pp. 1334-1339.

* cited by examiner

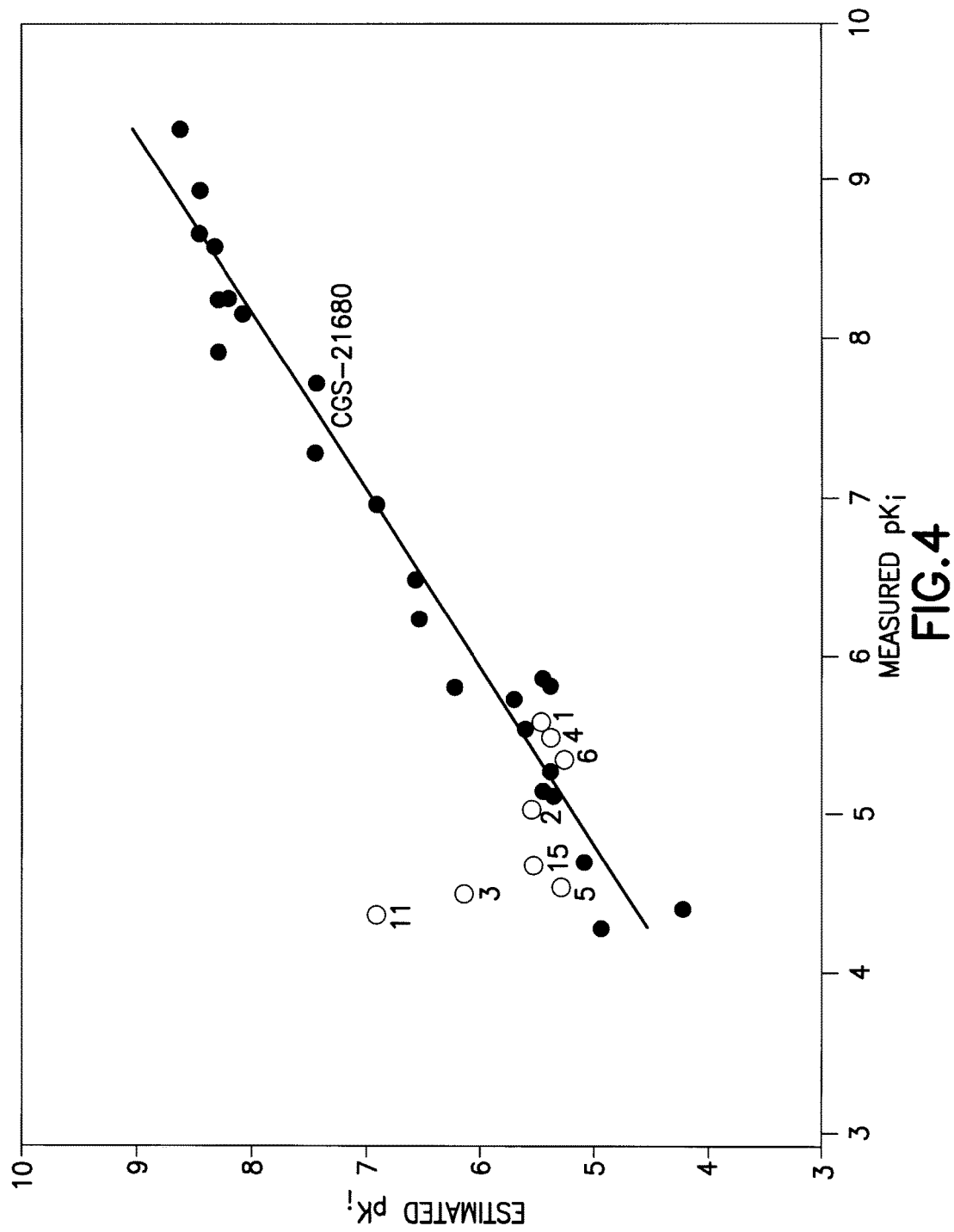

DUAL-ACTION COMPOUNDS TARGETING ADENOSINE $A_{2A}$ RECEPTOR AND ADENOSINE TRANSPORTER FOR PREVENTION AND TREATMENT OF NEURODEGENERATIVE DISEASES

REFERENCE TO RELATED APPLICATION

This application is a division and claims priority to U.S. application Ser. No. 13/508,797 filed May 9, 2012, which is a national stage application (under 35 U.S.C. 371) of PCT/US2010/056516 filed on Nov. 12, 2010, which claims priority to U.S. Provisional application Ser. No. 61/260,932 filed Nov. 13, 2009, all of which are herein incorporated by reference in their entireties.

TECHNICAL FIELD

The present invention provides the identification, synthesis and use of compound active for treating neurodegenerative diseases, such as Huntington's disease.

ABBREVIATIONS $A_{2A}R$, $A_{2A}$ adenosine receptor; $Ac_2O$, acetic anhydride; CGS, 6-amino-9-(5-ethylcarbamoyl-3,4-dihydroxy-oxolan-2-yl)-2-{2-[4-(2-carboxyethyl)phenyl]ethylamino}purine; DIEA, diisopropylethylamine; DMF, N,N-dimethylformamide; DML, designed multiple ligands; ENT, equilibrative nucleotide transporter, ESI, electrospray ionization; EtOAc, ethyl acetate; HD, Huntington's disease; hENT1, human equilibrative nucleoside transporter 1; HBA, hydrogen bond acceptor; HED, hydrogen bond donor; HBTU. 2-(1H-benzotriazol-1-yl)-1,1,3,3-tetramethyluronium; HOBt, 1-hydroxybenzotriazole; HP, hydrophobic; HPLC, high-performance liquid chromatography; IR, infrared; JNK, c-Jun N-terminal kinase; MS, mass spectrometry; MsCl, methanesulfonyl chloride; MTT, 3-(4,5-dimethylthiazol-2-yl)-2,5-diphenyltetrazolium bromide; NBTI, S-(4-nitrobenzyl)-6-thioinosine; NMR, nuclear magnetic resonance; py, pyridine; PyBOP, benzotriazol-1-yl-oxytripyrrolidinophosphonium hexafluorophosphate; RA, ring aromatic; t-BuOH, tertiary butanol; TEMPO, 2,2,6,6-tetramethylpiperidinyl-1-oxy; THF, tetrahydrofuran; TLC, thin-layer chromatography; TsCl, p-toluenesulfonyl chloride; TsOH, p-toluenesulfonic acid; ZM, 4-(2-[7-Amino-2-{2-furyl}{1,2,4}triazolo{2,3-a}{1,3,5}triazin-5-yl-amino]ethyl) phenol.

BACKGROUND ART

Introduction

Huntington's disease (HD) is an autosomal dominant neurodegenerative disease caused by a CAG trinucleotide expansion in the Huntingtin (Htt) gene, which shows chorea, dementia, and psychiatric symptoms.[1-3] Effective treatment for HD has not yet been developed, though a few therapeutic agents with moderate effects have been reported.[4,5] It has been demonstrated that the selective $A_{2A}$ adenosine receptor ($A_{2A}R$) agonist, CGS21680 (in short, CGS), can attenuate the HD symptoms in a transgenic mouse model,[6] and this compound has been shown to be able to rescue the urea cycle deficiency of HD disease by enhancing the activity of the ubiquitin-proteasome system.[7] However, CGS is known to exert strong immunosuppressive effect,[8] among other side effects, and therefore is not suitable for clinical use. On the other hand, an adenosine analogue, designated as T1-11 (compound 1), also an $A_{2A}R$ agonist, is recently isolated from *Gastordia elata* and shown to prevent serum-derived PC12 cell apoptosis, suggesting its therapeutic potential in treating neural degenerative diseases.[9]

SUMMARY OF THE INVENTION

It has been recognized that the $A_{2A}R$ and the adenosine transporter (such as the equilibrative nucleoside transporter ENT1) are both localized in the striatum,[10-13] where the mutant Htt aggregate.[14] Inhibition of the adenosine transporter would elevate the local concentrations of adenosine, and thereby increases the efficacy in agonizing the $A_{2A}R$. Interestingly, compound 1 is also found to be an ENT1 inhibitor. On the other hand, the potent immunosuppressant effect of CGS was a consequence of $A_{2A}R$ signaling,[8] which indicates that extremely strong binding affinity to $A_{2A}R$ may not be a desirable property for clinically useful therapeutic agents. It is therefore of considerable interest to modify compound 1 yet to retain its multiple-action property. Besides, transient or weakly binding compounds may be preferable than stably binding compounds,[15] especially when targeting the $A_{2A}R$ signaling system due to the aforementioned reasons. Designed multiple ligands (DML)[16,17] are conceptually distinct from promiscuous compounds discovered by random screening, because they are rationally designed to optimize the desired properties. It has been proposed that DMLs may be advantageous for treatment of diseases with complex etiologies, e.g., asthma, obesity, cancer, and psychiatric diseases, compared to the individually-targeting compounds.[16-18] It has been conceived that the intrinsic redundancy and robustness of complex biological networks may be responsible to the failure of highly selective drugs to deliver the intended therapeutic effects.[19] A recent assessment indicates that $A_{2A}R$ pharmacology is indeed rather complex,[20] and therefore DMLs may be especially suitable for targeting the $A_{2A}R$ signaling system. However, to design multiple-targeting ligands is often a challenging task,[21,22] partly due to the difficulty in appropriate construction of the computational models for describing the interactions of the ligands with several targets, and partly due to the increased restraints of chemical synthesis, and satisfaction of physical chemical properties of compounds. Perhaps associated with the increasing complexity as the number of targets increases, currently most of reported DMLs are dual-function ligands.[22] We have described in our previously filed provisional application, U.S. Provisional Patent Application 61/260,932, a number of compounds that have been synthesized and that exhibit dual functions on both adenosine receptors and transporters. These are generally described as compounds having an adenosine structural scaffold with variations at C-6 and C-5' with the following structure

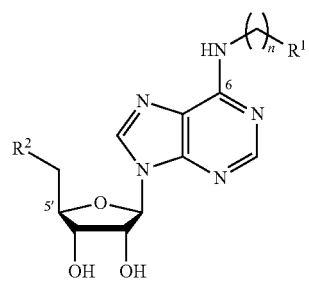

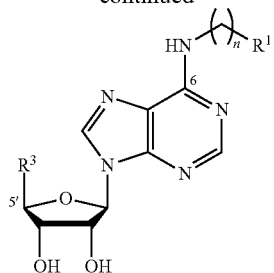

wherein n is 1 to 3, $R^1$ selected from the group consisting of (substituted)-benzene, polyarene and heterocycle, $R^2$ is selected from the group consisting of halogen, hydroxyl, alkoxy, azido, amino, (substituted)amino, amido, sulfanyl, sulfonyl, triazolyl, and cyano groups, and $R^3$ is selected from the group consisting of (substituted)carbonyl, carboxylate, (substituted)carbamide, cyano, (substituted)alkynyl, and (substituted)tetrazole groups.

Preferably, the compounds of one embodiment of the present invention have the structure of

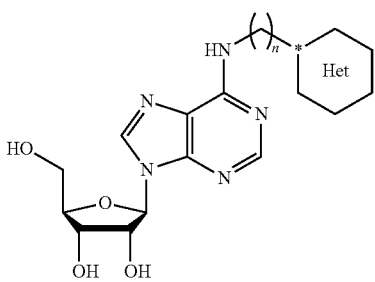

wherein the (substituted) heterocycle contains 5- or 6-membered rings and the fused heterocycle contain nitrogen, oxygen or sulfur heteroatoms and the substituents is selected from the group consisting of hydrogen, halogen (fluorine, chlorine, bromine and iodine), hydroxy, alkyl (1 to 6 carbons), trifluoromethyl, and (substituted)phenyl group.

The heterocycle may be pyrrole, furan, thiophene, pyridine, piperidine, piperazine, indole, benzofuran, benzothiophene, or quinoline. Another preferable embodiment are compounds having the structure of

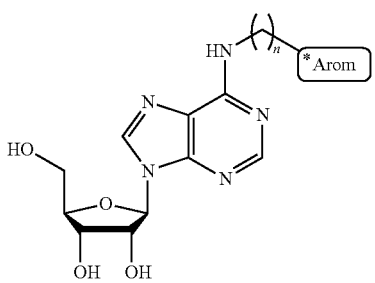

Wherein the aromatic ring is selected from the group consisting of benzene, naphthalene, anthracene, phenanthrene, and pyrene; when n=1, the benzyl group may optionally have substituents selected from the group consisting of halogen (fluorine, chlorine, bromine and iodine), alkyl (methyl, ethyl, propyl, butyl and trifluoromethyl), phenyl, hydroxy, alkoxyl (OR where $R=CH_3$, $C_2H_5$, $C_3H_7$ and $C_4H_9$), amino (NRR' where R, R' represent H, $CH_3$, $C_2H_5$, $C_3H_7$, $C_4H_9$, and phenyl), amido (NHCOR where $R=CH_3$, $C_2H_5$, $C_3H_7$ and $C_4H_9$), nitro, sulfonate, alkanoyl (COR where $R=H$, $CH_3$, $C_2H_5$, $C_3H_7$, $C_4H_9$ and phenyl), and carboxylate ($CO_2R$ where $R=H$, $CH_3$, $C_2H_5$, $C_3H_7$, $C_4H_9$ and phenyl).

Preferably, the compound has the structure of

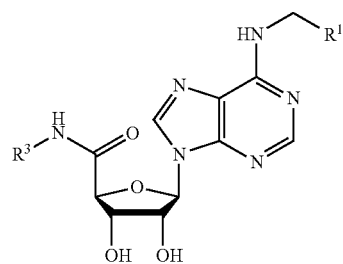

wherein $R^3$ is selected from the group consisting of hydrogen, alkyl (1 to 4 carbons), and (substituted)phenyl groups, and $R^1$ is as described above.

Another preferable compound has the structure of

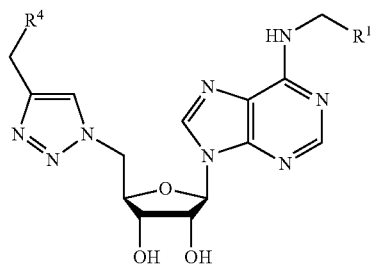

wherein $R^4$ is selected from the group consisting of hydrogen, halogen (fluorine, chlorine, bromine and iodine), hydroxy, alkyl (1 to 6 carbons), trifluoromethyl, and (substituted)phenyl group, and $R^1$ is as described above.

Still another preferable compound has the structure of

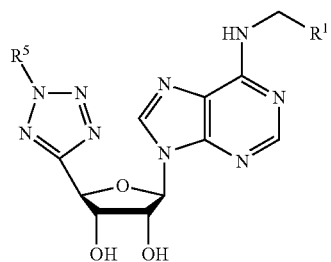

wherein R is selected from the group consisting of hydrogen and alkyl (1 to 4 carbons) groups, and $R^1$ is as described above.

Another preferable compound has the structure of

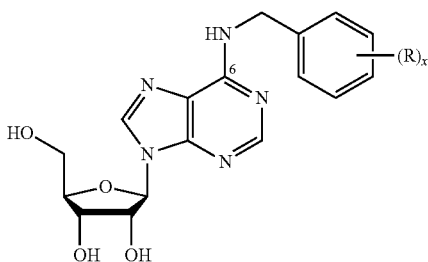

wherein R is selected from the group consisting of H, halogen (F, Cl, Br, and I), alkyl (1 to 4 carbons, trifluoromethyl, phenyl, hydroxyl, alkoxy (1 to 4 carbons), (substituted)amino, (substituted)amido, nitro, sulfonate, carbonyl, and carboxylate groups located at ortho-, meta- or para-positions, and wherein x is 1 to 5.

The present invention, in another embodiment, provides a method for treating neurodegenerative disease, comprising administering to a subject in need thereof an effective amount of at least one of the compounds discussed above. The neurodegenerative disease may be a protein-misfolding disease which is defined as a disease caused by protein-misfolding. These protein-misfolding diseases include Alzheimer's disease, Parkinson's disease, amyotrophic lateral sclerosis, Prion disease, Huntington's disease, and spinal Cerebellar ataxias. The present method is especially useful in treating Huntington's disease.

As another embodiment, the present invention provides for a composition comprising an effective amount of at least one of the above described compounds and a pharmaceutically acceptable carrier.

To rationally design the proper dual-action ligands as therapeutics for Huntington's disease, we first constructed two pharmacophore models, one for the $A_{2A}R$ agonists, and the other for the ENT1 inhibitors. Three-dimensional pharmacophores are specific spatial distributions of chemical functional features of a series of compounds that target the same active site of a biomolecule and exert the same function,[23] which are particular useful if the high resolution X-ray or NMR structures of the target biomolecules are not yet available. Pharmacophore analysis has been successfully applied to numerous drug discovery tasks.[24-29] Although the high resolution crystal structure of human adenosine $A_{2A}$ receptor has been released recently,[30] it represents the conformation bound with the antagonist ZM241385 (in short, ZM), not with an agonist. On the other hand, the crystal structure of human ENT1 (hENT1) is not yet available, and there is also no suitable structural template for homology modeling.

Based on the structural scaffold of 1, we set out to design a series of adenosine derivatives (FIG. 1). Chemical modifications of adenosine were carried out if the pharmacophore fitting of the modified compound predicts acceptable activity. The competitive ligand binding assays were performed to verify if the designed compounds indeed bind to the $A_{2A}R$ and ENT1 with good affinity. Finally, these compounds were assayed whether they could prevent apoptosis of the serum-deprived PC12 cells, which is a crucial indication for their potential for treating neurodegenerative diseases.[31,32]

BRIEF DESCRIPTION OF THE DRAWINGS

FIG. 4 shows the scatter plot of the predicted $pK_i$ values of $A_{2A}$-PR agonists versus the measured $pK_i$ values. The filled circles represent the training compounds, and the open circles the synthesized compounds.

DESCRIPTION OF THE EMBODIMENTS

Pharmacophore Model of the Human Adenosine $A_{2A}$ Receptor Agonists

Figure 2A:
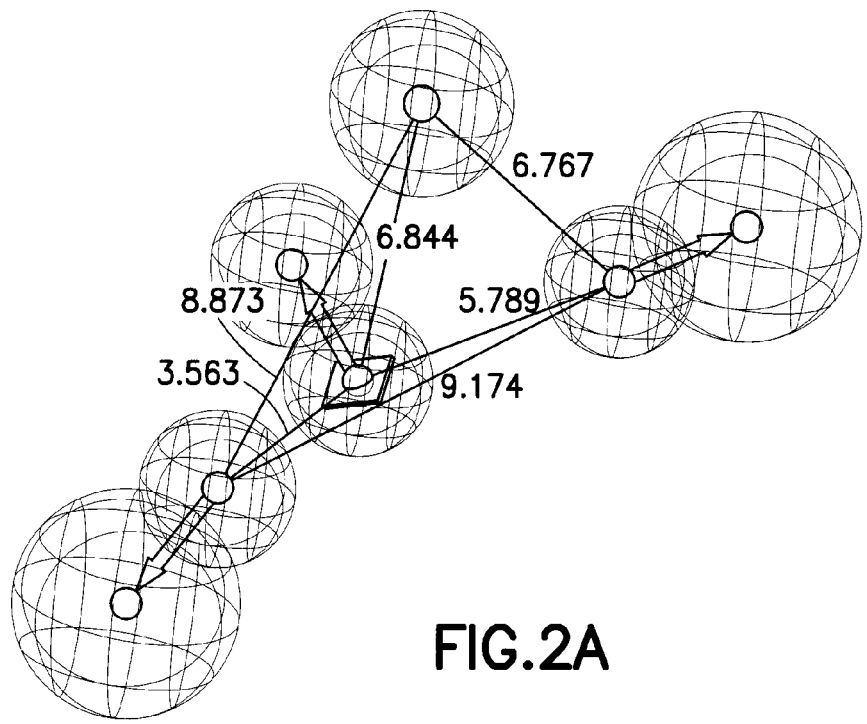
FIGS. 2A-F show the 3D pharmacophore model of the adenosine $A_{2A}$ receptor agonists. (A) The geometric features of the pharmacophore model. Cyan: hydrophobic (HP), gold: ring aromatic (RA), magenta: hydrogen bond donor (HBD), green: hydrogen bond acceptor (HBA) (B) Fitting of CGS into the pharmacophore model. (C) Fitting of compound 1. (D) Fitting of NBTI. (E) Fitting of compound 6. (F) Fitting of compound 11.
Figure 2B:
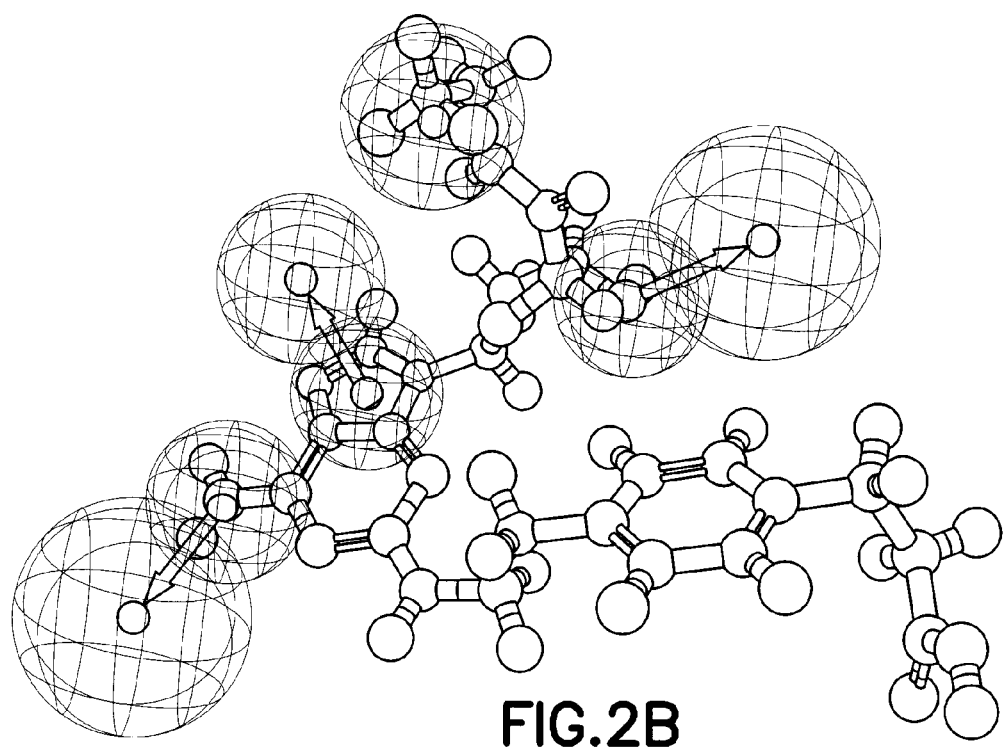
Figure 2C:
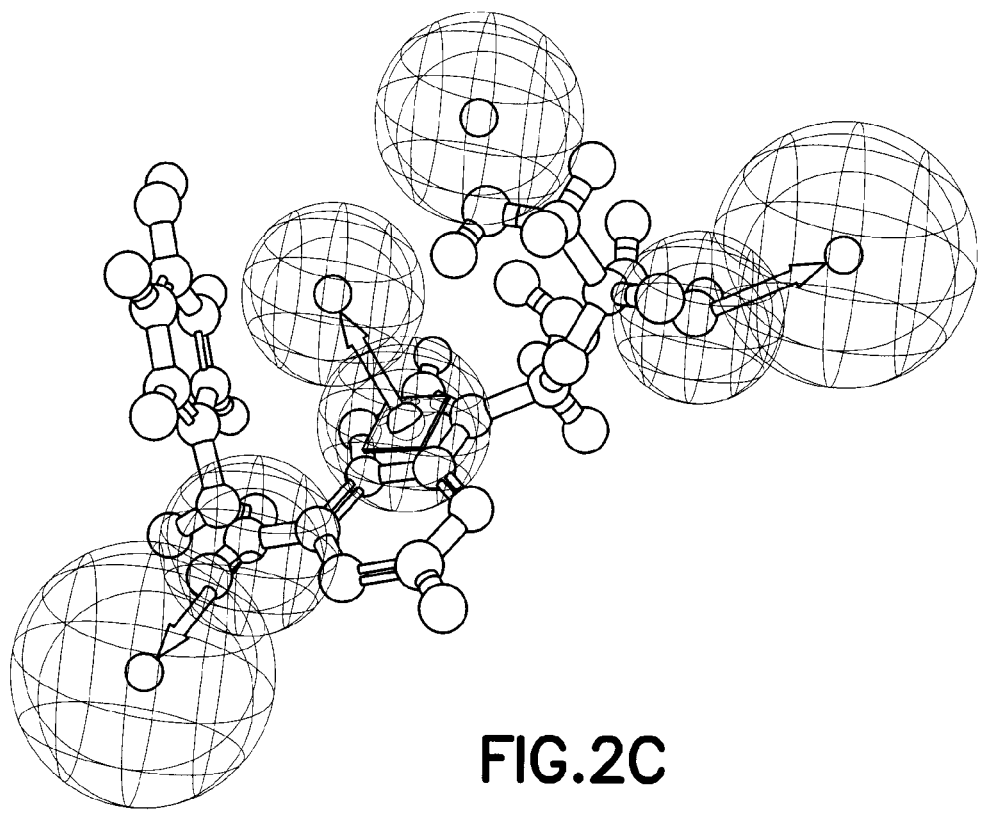
Figure 2D:
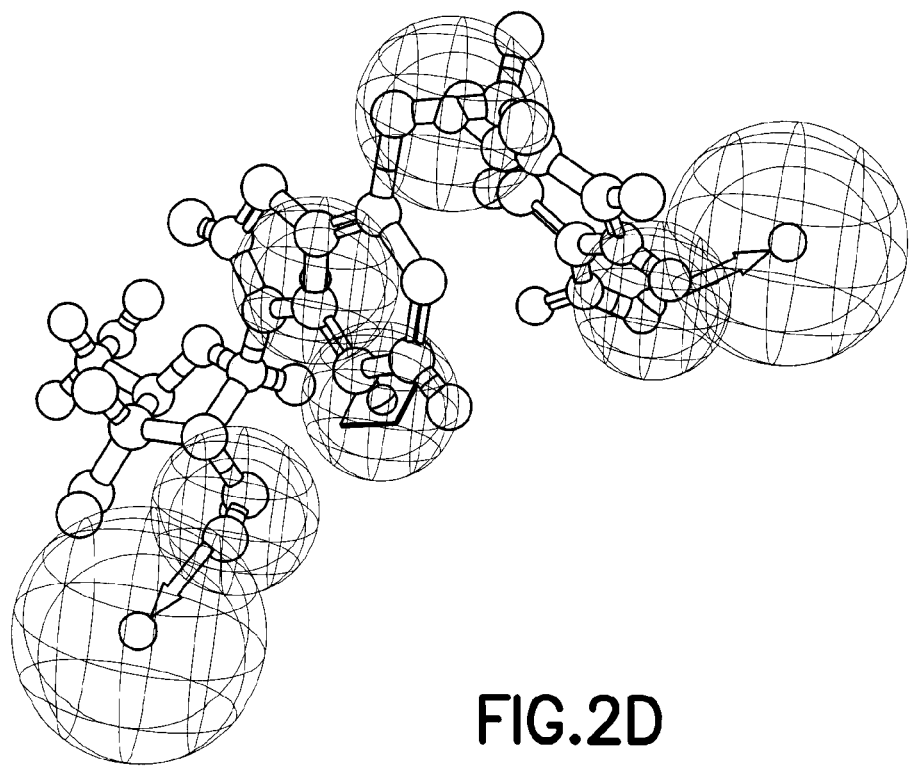
Figure 2E:
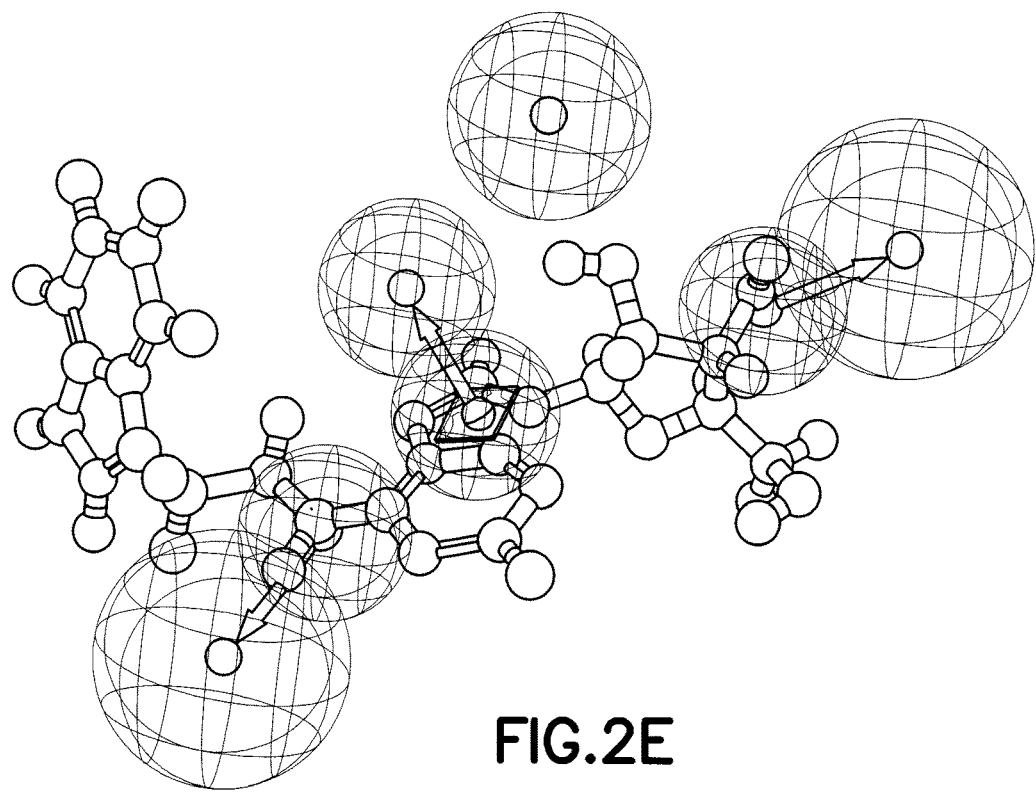
Figure 2F:
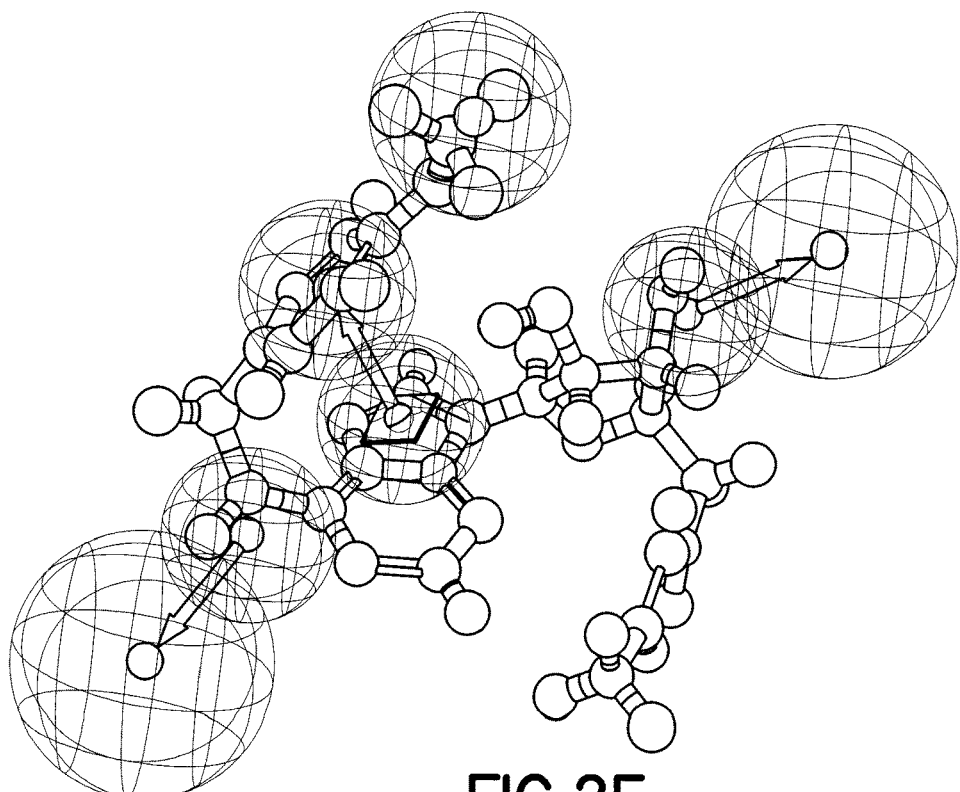

As part of the dual-pharmacophore drug design approach, a 3D-pharmacophore model of the human $A_{2A}R$ ($hA_{2A}R$) agonists was first constructed to design the compounds that could function as $hA_{2A}R$ agonists. The training set includes 25 compounds having large range of structural diversity and $hA_{2A}R$ activity ($K_i$ from 1.2 nM to 187 μM) selected from the literature. A potent $hA_{2A}R$ agonist CGS,[33] is also included in this training set. The HypoGen® module of Catalyst® of Accelrys®[34] was used to construct the pharmacophore model of these ligands. The constructed pharmacophore is illustrated in FIG. 2A, which shows four geometric features including hydrophobic (HP, in cyan), ring aromatic (RA, in gold), hydrogen bond donor (HBD, in magenta) and hydrogen bond acceptor (HBA, in green). For CGS all the four features of the constructed pharmacophore can be fitted nicely (FIG. 2B). In contrast, S-(4-nitrobenzyl)-6-thioinosine (NBTI)[35] lacks a ring-aromatic fitting (FIG. 2D), in agreement with its weak affinity as $hA_{2A}R$ ligand, though it exhibits a strong binding with adenosine transporter. The designed dual-action ligands 1, 6 and 11 fit at least three features in this pharmacophore model for $A_{2A}R$ agonists (FIGS. 2C, 2E and 2F).

Pharmacophore Model of the Equilibrative Nucleoside Transporter Inhibitors.

Figure 3A:
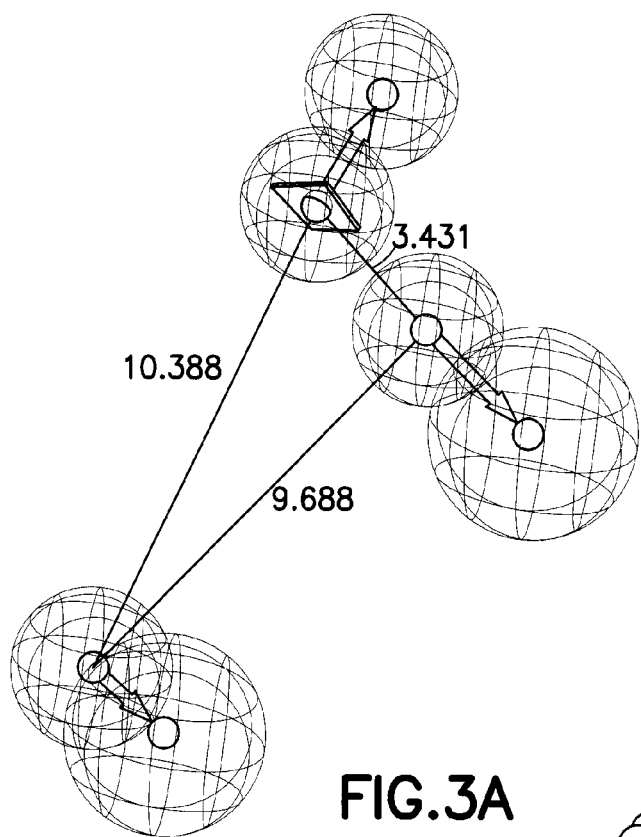
FIGS. 3A-F show the 3D pharmacophore model of the human equilibrative nucleoside transporter (hENT1) inhibitors. (A) The geometric features of the pharmacophore model. Gold: ring aromatic (RA), green: hydrogen bond acceptor (HBA1: 3.431 Å distance from RA; HBA2: 10.388 Å distance from RA). (B) Fitting of NBTI into the pharmacophore model. (C) Fitting of compound 1. (D) Fitting of CGS. (E) Fitting of compound 6. (F) Fitting of compound 11.
Figure 3B:
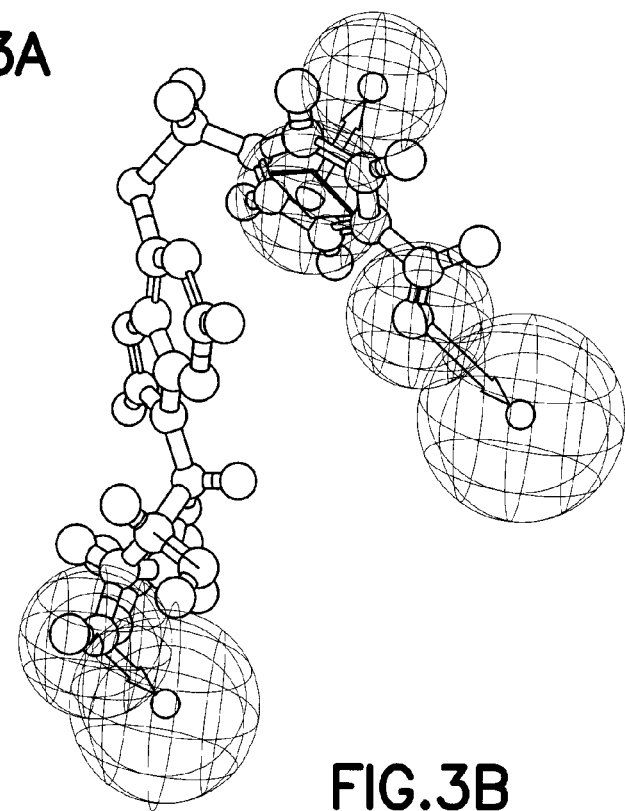
Figure 3C:
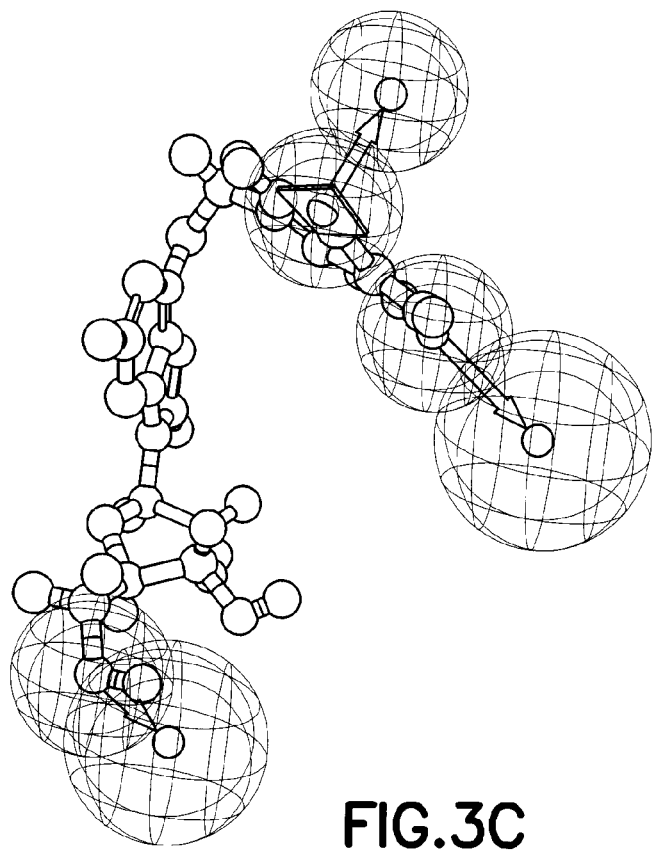
Figure 3D:
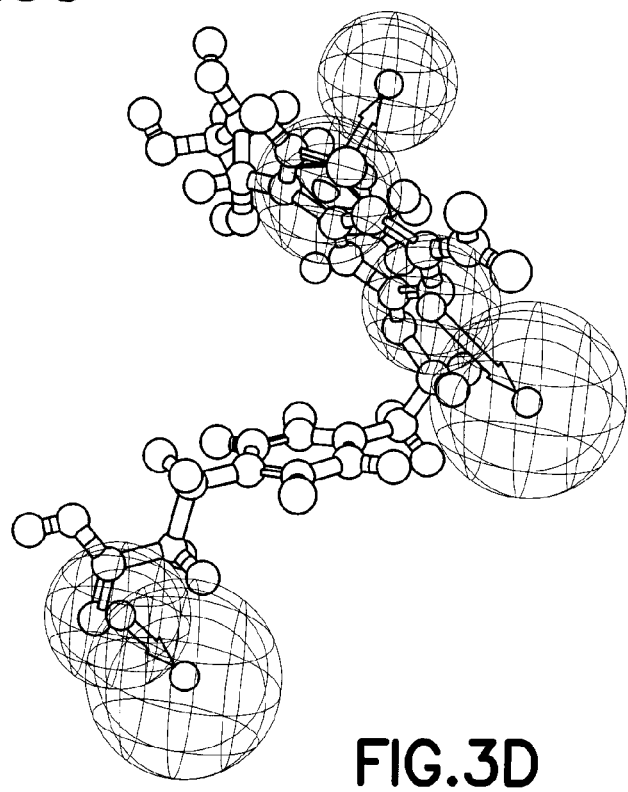
Figure 3E:
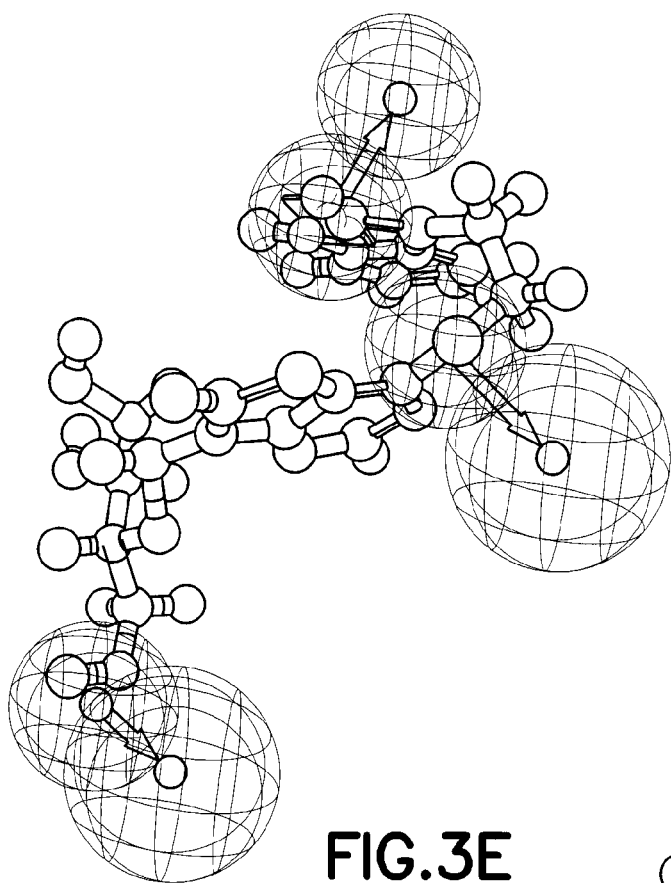
Figure 3F:
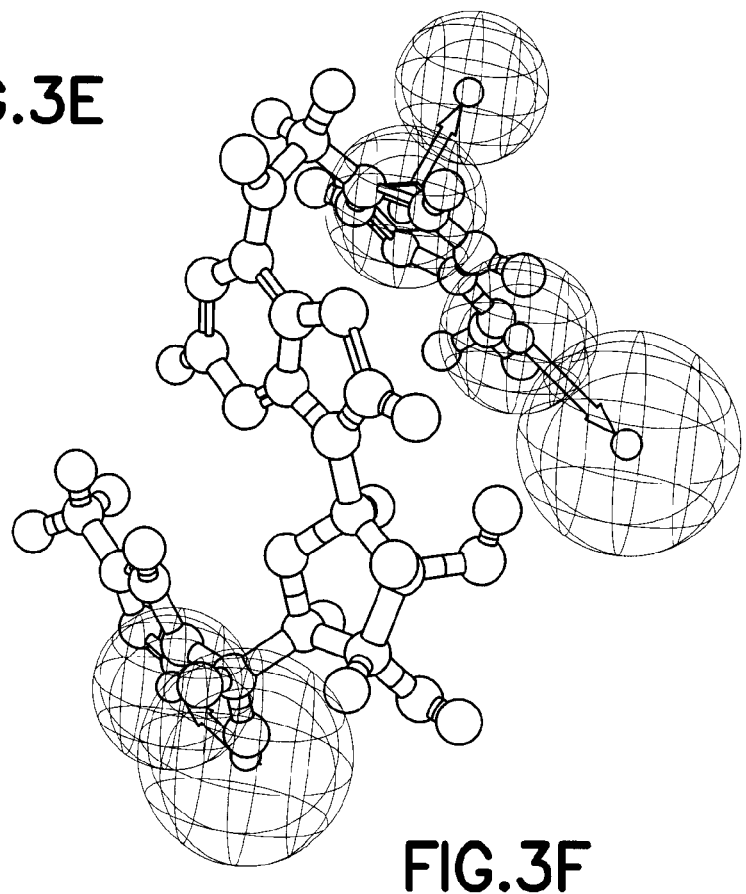

To design dual-function compounds that act cooperatively as the $hA_{2A}R$ agonists and the hENT1 inhibitors, the pharmacophore of hENT1 inhibitors was also constructed (FIG. 3A). The training set includes 25 compounds possessing hENT1 inhibitory activity ranging from $IC_{50}$ of 0.29 nM to 32 μM, which were selected from the literature (see Supporting information). The constructed pharmacophore model of the hENT1 inhibitors consists of only three features, including two hydrogen bond acceptors and one ring aromatic. All the five compounds (NBTI, 1, CGS, 6, and 11) can fit into all these three features (FIGS. 3B-F). The different number of features between the pharmacophores of hA$_{2A}$R agonists and hENT1 inhibitors could be attributed to the nature of the training set compounds.

By carefully scrutinizing the structures in the hA$_{2A}$R agonists training set (see Supporting Information), we found that many of them possess a hydrophobic group in the 5' end of nucleoside, especially those compounds with higher potency, including CGS. Therefore, the constructed pharmacophore must include this important feature. On the contrary, in the hENT1 inhibitors training set, almost all the 5' end of the nucleoside possesses a polar hydroxyl group.

The pharmacophore differences among the two investigating targets also shed some light on the design of dual-function compounds. For example, compound 6 does not fit well to the hydrophobic feature in hA$_{2A}$R receptor pharmacophore model, and it is indeed less potent than CGS, which fits well to all features. However, compound 6 could fit well in all three features in hENT1 model.

As for compound 11, it fits well to all features including hydrophobic of A$_{2A}$R pharmacophore mode. Nevertheless, it still fits well to hENT1 pharmacophore model, indicating the higher tolerance of ENT1 pharmacophore model. In summary, by comparing the features and compound-fitting qualities of these two pharmacophore models, we may hypothesize that the hA$_{2A}$R binding pocket has an important hydrophobic site, and the hENT1 binding pocket may be more flexible to accommodate the nucleosides with hydrophobic moieties at the 5' end in this series of compounds. Pharmacophore analyses provide us with an insight into the design and understanding of dual-function compound in the absence of the structural information of hENT1.

Synthesis of Adenosine Derivatives.

Figure 1:
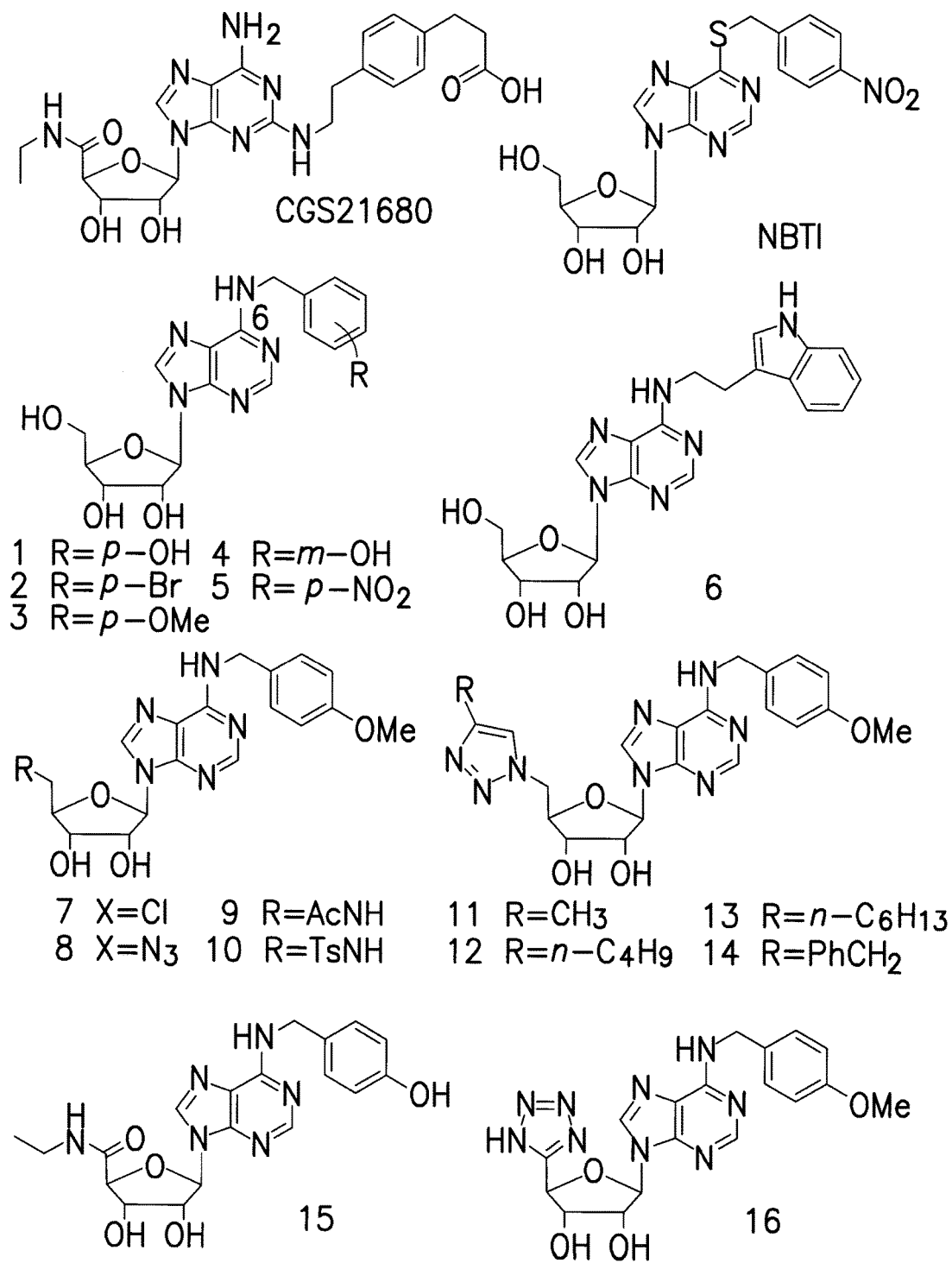
FIG. 1 shows structures of CGS, NBTI and some designed adenosine derivatives with modification at the $N^6$- and $C^{5'}$-positions.

A representative library of adenosine analogues (FIG. 1) was developed based on the pharmacophore models. Compound 1, originally isolated from *Gastrodia elata*,[3] was synthesized in a high yield by the substitution reaction of 6-chloropurine ribofuranoside (17) with 4-hydroxybenzylamine (as the hydrochloric salt) in the presence of a base of diisopropylethylamine. As 4-hydroxybenzylamine was not commercially available, it was prepared in two steps from 4-hydroxybenzaldehyde via the condensation reaction with hydroxylamine to give an intermediate oxime, which was subsequently hydrogenated by the catalysis of Pd/C and HCl. By the procedures similar to that for compound 1, a series of N$^6$-substituted adenosine derivatives 2-6 were prepared by the substitution reactions of 6-chloropurine ribofuranoside with appropriate substituted benzylamines. In lieu of the conventional heating method, microwave irradiation was also applied to shorten the reaction time in the preparation of N$^6$-(3-indolylethyl)adenosine (6).

Scheme 1. Synthesis of N$^6$-(4-methoxybenzyl) adenosine (3) and substitution of its 5'-hydroxy group with chlorine, azide, acetamide, and p-toluenesulfonamide.

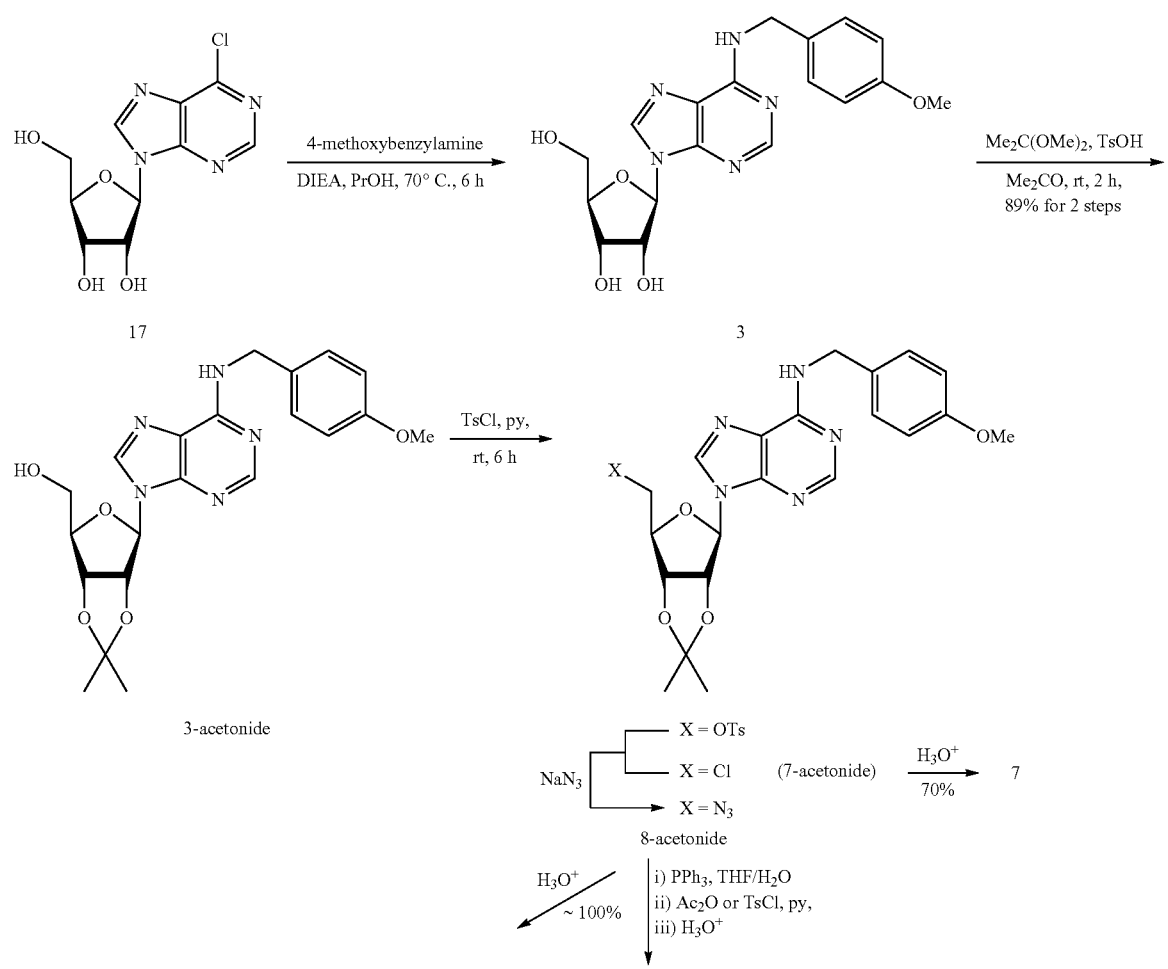

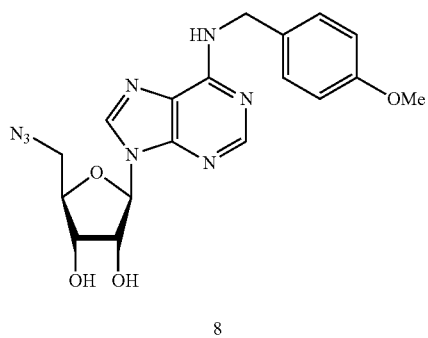

8

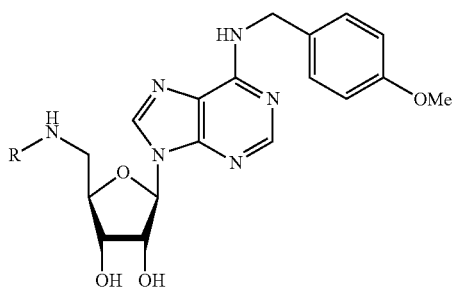

9 R = Ac
(8% from 3-acetonide)
10 R = Ts
(7% from 3-acetonide)

Treatment of N⁶-(4-methoxybenzyl)adenosine 3 with 2,2-dimethoxypropane in anhydrous acetone afforded the corresponding 3-acetonide, which reacted with p-toluenesulfonyl chloride in the presence of pyridine to give a mixture of tosylate and chloride derivatives (Scheme 1). The tosylate derivative was unstable, whereas the chloride compound (7-acetonide) could be isolated by chromatography and subsequently hydrolyzed to give 7. Without separation, this mixture was treated with sodium azide, followed by acid-catalyzed hydrolysis, to give an azido compound 8. Alternatively, Staudinger reduction of 8-acetonide gave an intermediate amine, which was converted to the corresponding acetamide 9 and sulfonamide 10 after removal of the 2',3'-isopropylidene group in acid.

Scheme 2. Elaboration of the 5'-azido group by click reaction to give triazole compounds.

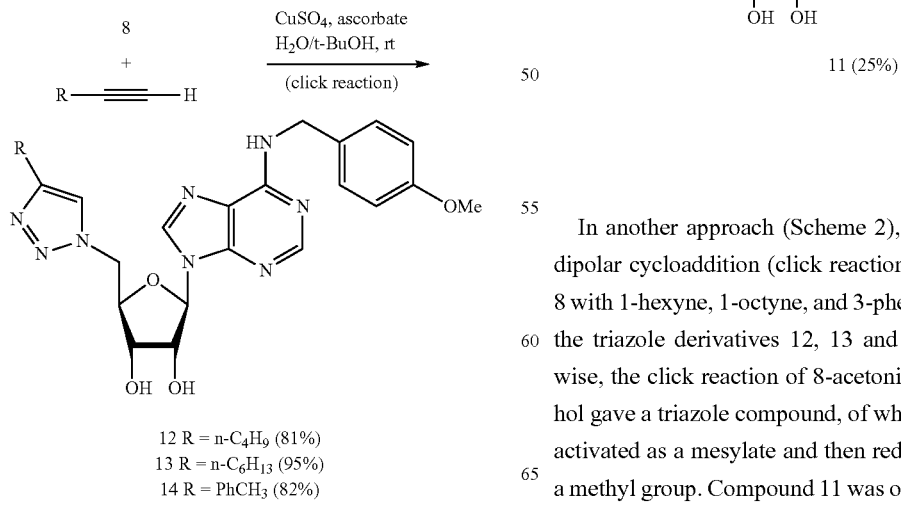

12 R = n-C₄H₉ (81%)
13 R = n-C₆H₁₃ (95%)
14 R = PhCH₃ (82%)

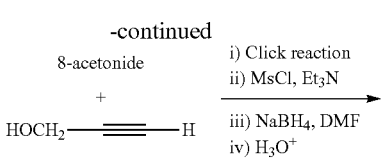

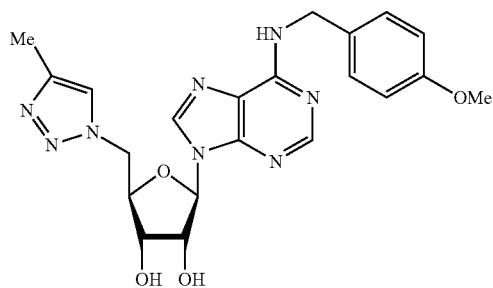

11 (25%)

In another approach (Scheme 2), the Cu⁺-catalyzed 1,3-dipolar cycloaddition (click reaction)[38] of azido compound 8 with 1-hexyne, 1-octyne, and 3-phenyl-1-propyne afforded the triazole derivatives 12, 13 and 14, respectively. Likewise, the click reaction of 8-acetonide with propargyl alcohol gave a triazole compound, of which hydroxyl group was activated as a mesylate and then reduced by NaBH₄ to give a methyl group. Compound 11 was obtained after removal of the 2',3'-isopropylidene group.

Scheme 3. Synthesis of carboxamide and tetrazole derivatives.
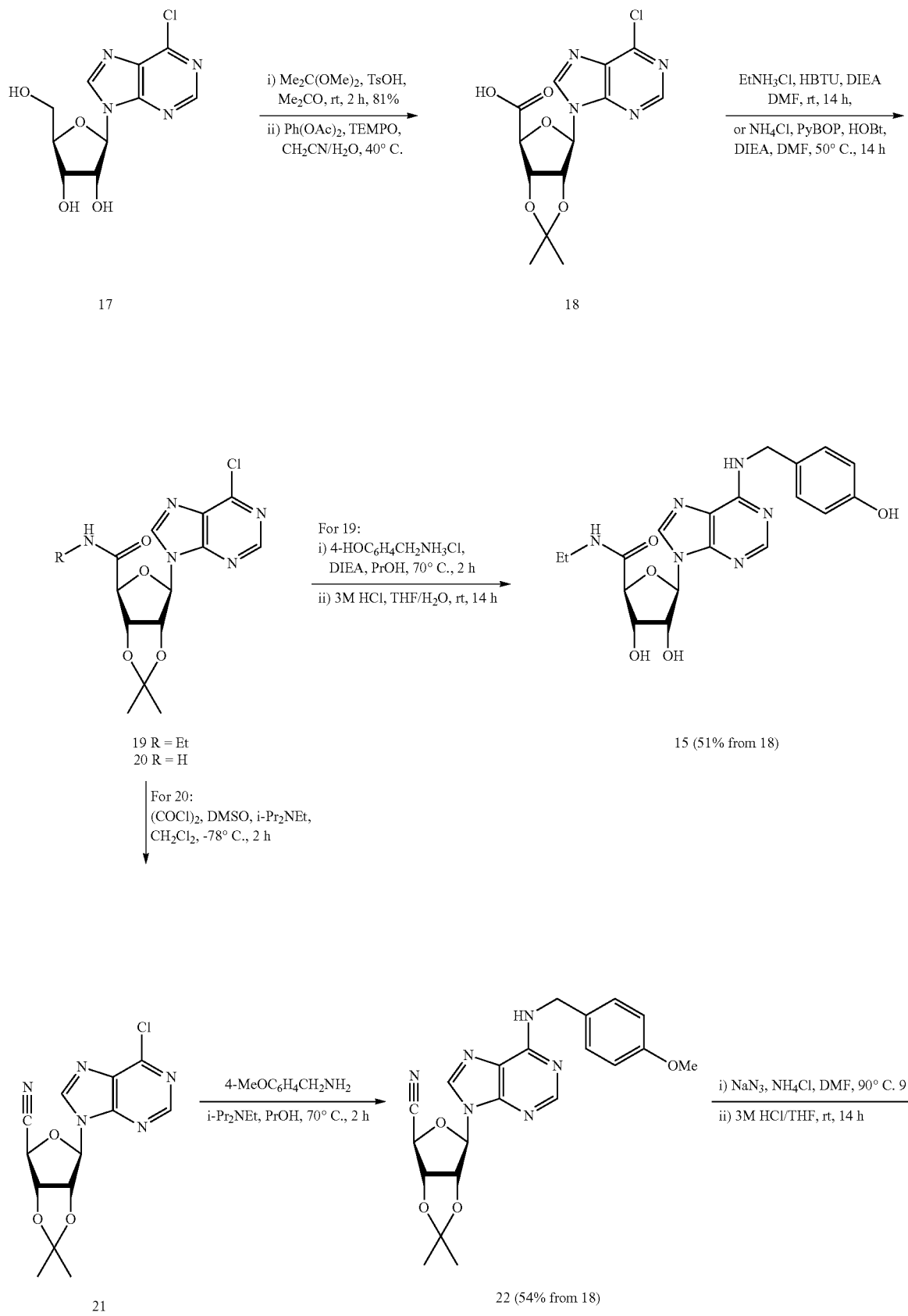

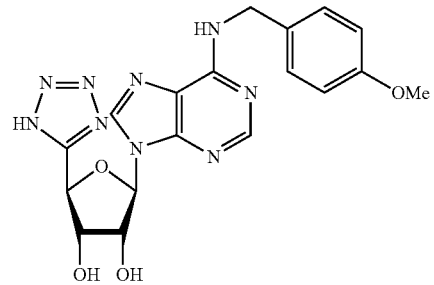

16 (35% from 18)

The acetonide of 6-chloropurine ribofuranoside was oxidized by (diacetoxyiodo)benzene with catalysis of 2,2,6,6-tetramethylpiperidinyl-1-oxy (TEMPO)[39] to give a carboxylic acid 18. The coupling reactions of acid 18 with ethylamine and ammonia gave amides 19 and 20, respectively. The chlorine atom in 19 was replaced by 4-hydroxybenzylamine, and the subsequent hydrolysis of the acetonide furnished amide 15. On the other hand, amide 20 was converted to nitrile 21 on treatment with $Me_2SO$, oxalyl chloride and i-$Pr_2NEt$.[40] After the chlorine atom was substituted by 4-methoxybenzylamine, a 1,3-dipolar cycloaddition of the cyano group with $NaN_3$ introduced the desired tetrazole moiety at the C-5' position,[41] giving 16 after removal of the 2',3'-isopropylidene group under acidic conditions.

Biological Evaluation of $N^6$- and $C^{5'}$-Modified Adenosine Derivatives.

The pharmacological properties of the prepared adenosine analogues were characterized by MDS Pharma Services using radioligand binding assays. The binding constants ($K_i$) of some representative compounds are shown in Table 1. The potent $A_{2A}R$ agonist CGS appears to lack the activity against ENT1, whereas the ENT1 inhibitor NBTI shows no binding ability with $A_{2A}R$. Neither CGS nor NBTI is dual-functional drug. Some prepared adenosine analogues exhibit the dual actions on $A_{2A}R$ and ENT1, in particular, compounds 1, 4 and 6 showing the $K_i$ values in low micromolar and sub-micromolar range with $A_{2A}R$ and ENT1, respectively. Except for 11 and 15, the adenosine derivatives having modification at the C-5' position appeared to deteriorate their binding with $A_{2A}R$, though they still maintained high affinity with ENT1.

TABLE 1

Binding activity of the $N^6$- and $C^{5'}$-modified adenosine derivatives with adenosine receptor and transporter.[a]

| | $K_i$ (μM) | |
| Compound | $A_{2A}$-$R^b$ | ENT1[c] |
| --- | --- | --- |
| CGS | $7.77 \times 10^{-2}$ | — |
| NBTI | >10 | $2.9 \times 10^{-4}$ |
| 1 | 2.62 | $5.38 \times 10^{-1}$ |
| 1-acetonide | >100 | >100 |
| 2 | 14.4 | $1.44 \times 10^{-2}$ |
| 3 | 30.1 | $3.18 \times 10^{-1}$ |
| 4 | 3.21 | 3.72 |
| 5 | 27.7 | $6.51 \times 10^{-3}$ |
| 6 | 4.39 | 3.47 |
| 7 | >100 | 2.98 |
| 8 | — | $5.81 \times 10^{-1}$ |
| 9 | >100 | 1.43 |

TABLE 1-continued

Binding activity of the $N^6$- and $C^{5'}$-modified adenosine derivatives with adenosine receptor and transporter.[a]

| | $K_i$ (μM) | |
| Compound | $A_{2A}$-$R^b$ | ENT1[c] |
| --- | --- | --- |
| 10 | >100 | $2 \times 10^{-1}$ |
| 11 | 41.8 | $9.60 \times 10^{-1}$ |
| 12 | >100 | $5.11 \times 10^{-1}$ |
| 13 | >100 | $5.2 \times 10^{-2}$ |
| 14 | >100 | $1.16 \times 10^{-1}$ |
| 15 | 20.3 | >10 |
| 16 | >100 | 1.17 |

[a]The radioligand binding assays were performed by MDS Pharma Services Taiwan (Taipei, Taiwan) using standard binding protocols.
[b]Human adenosine $A_{2A}$ receptor.
[c]Guinea pig equilibrium transporter 1.

We have previously reported that compound 1 isolated from an aqueous methanolic extract of *Gastrodia elata* prevented apoptosis of serum-deprived PC12 cells by suppressing JNK activity.[15] In this study, serum-deprived PC12 cells were treated with the compound at the indicated dose for 24 h. Cell viability was monitored by the MTT assay, and is expressed as a percentage of the MTT activity measured in the serum-containing group. At a concentration of 0.01 μM, compounds 4 and 6 also rescued PC12 cells from the apoptosis evoked by serum withdrawal equally as well as 1 according to the cell viability of MTT assays. Collectively, the dual function of these compounds in activation of adenosine receptor and in inhibition of adenosine transporter might synergistically increase the effective concentration of adenosine, especially when these two proteins are in proximity.

Statistical Assessment of Pharmacophore Models.

FIG. 4 shows the scatter plot of the experimental $pK_i$ versus predicted $pK_i$ values from the pharmacophore model of $A_{2A}R$ agonists. The $r^2$ value of the predicted $K_i$ values versus the experimental $K_i$ values is 0.962, and the root-mean-square of error (rmse) is 0.658 kcal/mol. This pharmacophore model was further evaluated using the Fisher's randomization test for statistical significance, as implemented in the CatScramble module. The CatScrambler module scrambled the $pK_i$ values randomly for 19 times to generate new hypotheses (i.e., pharmacophore models). None of the 19 hypotheses from the scrambled data had a cost lower than the reported hypothesis. Table 2 summarizes the fitted features of the compounds in FIG. 4, along with the distance deviation of the fitted location of the feature on the compound from the center of the feature in the pharmacophore model. To reiterate, Table 2 is a quantitative representation of FIG. 4. When a ligand is fitted into a pharmacophore, the quality of fitting (or mapping) is indicated by the "fit value." A higher fit value represents a better fit, and the computer fit values depends on two factors: the weights assigned to the pharmacophore features and how close the features in the molecules are to the exact locations of the features in the pharmacophore model.

TABLE 2

Comparison of activities of compounds with the fitted number of features of the $A_{2A}$-R agonist pharmacophore model. The numbers are in the unit of Å.

| Compound ID | HBD | HBA | RA | HP | Fit Value |
|---|---|---|---|---|---|
| CGS21680 | √/0.166 | √/0.125 | √/0.201 | √/0.436 | 10.6482 |
| 1 (T1-11) | √/0.121 | √/0.135 | √/0.248 | x | 8.68049 |
| NBTI | √/0.422 | √/0.304 | x | √/0.901 | 8.62848 |
| 6 | √/0.377 | √/0.359 | √/0.403 | x | 8.52907 |
| 11 | √/1.181 | √/0.445 | √/0.434 | √/0.544 | 9.59155 |

The potent $A_{2A}$R agonist CGS fits all the four features of the constructed pharmacophore, and the deviations of the fitted feature locations from the exact locations of the features of the pharmacophore model are also very small. Compared to CGS, compound 1 lacks a hydrophobic moiety to fit into the feature of the pharmacophore model, and therefore exhibited a reduced affinity. In contrast, NBTI lacks a ring-aromatic moiety, which completely abolishes the activity to agonize the adenosine $A_{2A}$ receptor. This indicates that the ring-aromatic feature may be more important than the hydrophobic moiety in this pharmacophore model. Compound 6 does not fit the hydrophobic feature of the pharmacophore model, while compound 11 does show higher fit value. In contrast, the binding assays indicate that compound 6 ($K_i$=4.39 µM) exhibits 10-fold stronger binding affinity than compound 11 ($K_i$=41.8 µM). This can be rationalized by the fact that all the fitted locations of the features of the compound 6 have less deviations from the exact locations of the features.

Figure 5:
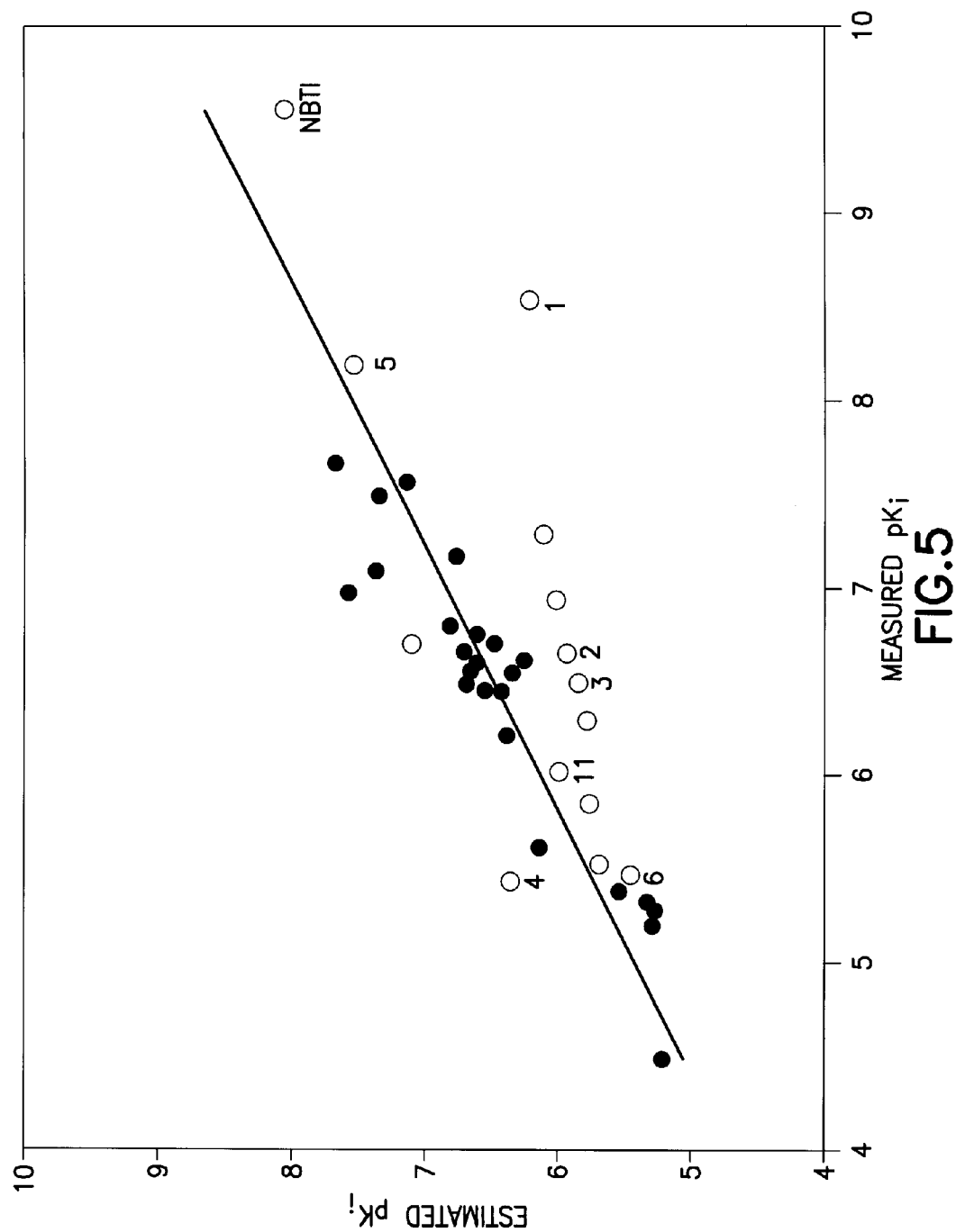
FIG. 5 shows the scatter plot of the predicted $pK_i$ values of ENT1 inhibitors versus the measured $pK_i$ values. The filled circles represent the training compounds, and the open circles the synthesized compounds.

The constructed pharmacophore model of the hENT1 inhibitors consists of only three features, namely, a ring aromatic feature and two hydrogen bond acceptors. The $r^2$ value of the predicted $K_i$ values versus the experimental $K_i$ values is 0.927, and the rmse is 0.85 kcal/mol (FIG. 5). This pharmacophore model was further evaluated by the CatScrambler module. All the five compounds (NBTI, 1, CGS, 6, and 11) can fit into all these three features (FIGS. 3B-F), and therefore the deviations from the exact locations of the features need to be compared (Table 3). Apparently, the most potent inhibitor, NBTI, has the highest fit value and smallest deviation of all three features. The fit values of compounds 1, 11 and 6 are 6.61, 6.4 and 5.86, respectively, which are consistent with the ranking of their measured activity. CGS (with a high fit value 7.1) is obviously an outlier of this model, since this compound has no inhibitory activity toward hENT1. However, CGS is the only compound with a ring aromatic feature fitted on to the nucleoside moiety (FIG. 3).

It is thus important to carefully examine whether the fitted functional group is indeed the same as the functional groups of the training set compounds that define the consensus feature in the pharmacophore analysis. The "fit value" alone can not be considered the measure of fitness.

TABLE 3

Comparison of activities of compounds with the fitted number of features of the ENT1 inhibitor pharmacophore model. The numbers are in the unit of Å.

| Compound ID | HBD | HBA | RA | Fit Value |
|---|---|---|---|---|
| NBTI | √/0.421 | √/0.647 | √/0.793 | 5.92748 |
| 1 | √/0.544 | √/0.619 | √/0.586 | 4.94133 |
| CGS21680 | √/0.567 | √/1.276 | √/0.358 | 5.37611 |
| 6 | √/0.421 | √/0.647 | √/0.493 | 5.40138 |
| 11 | √/0.74 | √/0.588 | √/0.942 | 4.35311 |

CONCLUSION

We have adopted a dual-pharmacophore modeling approach to design dual-action compounds targeting the $A_{2A}$R signaling system. Based on the structural scaffold of 1, we designed and synthesized a series of adenosine derivatives and carried out chemical modifications of adenosine if the pharmacophore fitting of the modified compound predicts acceptable activity. The competitive ligand binding assays verified that the designed compounds indeed bind to both $A_{2A}$R and ENT1 with moderate affinity. The effective amount of the designed compounds for therapeutic treatment of neurodegenerative diseases, including Huntington's disease, is 1.5-2.5 mg/kg, based on oral dosage of the representative T1-11 in mice. The preferred route of administration of the designed compounds is oral administration, either in immediate release or slow release forms. Finally, these compounds were shown to prevent apoptosis of the serum-deprived PC12 cells, which is a crucial indication for their potential for treating neurodegenerative diseases.

Experimental Section

Materials and Methods.

All reagents and solvents were of reagents grade and were used without further purification unless otherwise specified. Tetrahydrofuran and diethyl ether were distilled from Na/benzophenone and $CH_2Cl_2$ was distilled from $CaH_2$. All air or moisture sensitive experiments were performed under argon. All glasses were dried in oven for more than 2 hours and used after cooling to room temperature in desiccators. Microwave reactions were conducted using a focused single mode microwave unit (CEM Discover). The machine consists of a continuous focused microwave power delivery system with operator selectable power output.

Melting points were recorded on a Yanaco micro apparatus. Optical rotations were measured on digital polarimeter of Japan JASCO Co. DIP-1000. $[\alpha]_D$ values are given in units of $10^{-1}$ deg $cm^2$ $g^{-1}$. Infrared (IR) spectra were recorded on Nicolet Magna 550-II. NMR spectra were obtained on Varian Unity Plus-400 (400 MHz) and chemical shifts (δ) were recorded in parts per million (ppm) relative to $\delta_H$ 7.24/$\delta_C$ 77.0 (central line of t) for $CHCl_3/CDCl_3$, $\delta_H$ 2.05/$\delta_C$ 29.92 for $(CH_3)_2CO/(CD)_2CO$, $\delta_H$ 3.31/$\delta_C$ 49.0 for $CH_3OH/CD_3OD$, and $\delta_H$ 2.49 (m)/$\delta_C$ 39.5 (m) for $(CH_3)_2SO/(CD_3)_2SO$. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. Analytical thin-layer chromatography (TLC) was performed on E. Merck silica gel 60 $F_{254}$ plates (0.25 mm). Compounds were visualized by UV, anisaldehyde or ninhydrin spray. Column chromatography was carried out on columns packed with 70-230 mesh silica gel. Purity of compounds tested on $A_{2A}$-R and ENT1 was assessed to be ≥95% by HPLC (Agilent HP-1100) with detection at 280 nm wavelength.

Construction of Pharmacophore Models.

The HypoGen module of Catalyst® of Accelrys was used to construct the pharmacophore model of human $A_{2A}R$ agonists and human ENT 1 inhibitors. The chemical structures of the training set compounds and their binding affinities to the human $A_{2A}R$ (or human ENT 1) were collected from the literature (see Supporting information).[41-44] It is important to ensure that the activity of the training compounds cover at least four orders of magnitude, with at least three compounds in each log scale.[23,45] It is also recommended to select compounds with larger chemical diversity as the training set.[45] Each compound was sketched with ChemDraw, and then imported into Catalyst 4.11. The "Best" option was used for conformation generation. In Catalyst®, the Poling algorithm was used to generate 250 conformations, whose energies are less than 20.0 kcal/mol from the lowest energy of all the conformations. Five molecular features were selected, namely, hydrophobic (HPh), hydrogen bond acceptor (HBA), hydrogen bond donor (HBD), positively ionizable atom (PI), and negatively ionizable atom (NI). All these compounds were loaded into the Catalyst's spreadsheet and the default uncertainty of 3 were assigned. All other parameters are as default.

N[6]-(4-Hydroxybenzyl)adenosine (1).[9]

Hydroxylamine hydrochloride (1.29 g, 18.6 mmol) and sodium acetate (1.67 g, 20.4 mmol) were added to a solution of 4-hydroxybenzaldehyde (1.25 g, 10.2 mmol) in ethanol (20 mL). The reaction mixture was stirred at zoom temperature for 6 h. Ethanol was removed under reduced pressure. The residue was added water, and then extracted with $Et_2O$ (3×). The combined organic layer was dried over $MgSO_4$. After the volatiles were removed by rotary evaporation under reduced pressure, the residue was recrystallized from $CH_2Cl_2$ to give the oxime of 4-hydroxybenzaldehyde (1.3 g, 93%). $C_2H_7NO_2$; light yellow solid, mp 92.0-93.6° C.

A solution of the above-prepared oxime (342 mg, 2.5 mmol) and concentrated hydrochloric acid (1 mL) in ethanol. (20 mL) was subjected to hydrogenation at atmospheric pressure in the presence of 10% Pd/C (80 mg) for 4 h. The reaction mixture was filtered through Celite. The filtrate was concentrated to yield the hydrochloric salt of 4-hydroxybenzylamine as light yellow solids, which were used for the next step without further purification.

A mixture of 4-hydroxybenzylamine (395 mg, as the hydrochloric salt), 6-chloropurine riboside (143 mg, 0.5 mmol), and diisopropylethylamine (DIEA, 2 mL, 12 mmol) in 1-propanol (25 mL) was heated to 70° C. for 6 h. The mixture was concentrated under reduced pressure, and triturated with water to give white precipitates, which were filtered to yield the title compound 1 (151 mg, 81%). The purity of product was >99% as shown by HPLC on an Inertsil ODS-3 column (4.6×250 mm, 5 μm) with elution of 0.1% TFA/MeOH (6:4). $C_7H_{19}N_5O_9$; white powder, mp 208.7-209.2° C. (lit.[9] mp 216-219° C.); $[\alpha]^{20}_D=-64.5$ (DMSO, c=1) (lit.[9] $[\alpha]^{25}_D=-87$ (MeOH, c=0.1)); TLC (MeOH/EtOAc (1:9)) $R_f=0.3$; $^1H$ NMR (DMSO-$d_6$, 400 MHz) δ 9.22 (1H, s), 8.34 (1H, s), 8.30 (1H, br s), 8.18 (1H, s), 7.12 (2H, d, J=8.0 Hz), 6.65 (2H, d, J=8.0 Hz), 5.86 (1H, d, J=5.6 Hz), 5.41 (2H, m), 5.18 (1H, d, J=5.6 Hz), 4.60 (2H, m), 4.13 (1H, q, J=4.6, 7.4 Hz), 3.95 (1H, q, J=3.4, 6.2 Hz), 3.66 (1H, m), 3.53 (1H, m); $^{13}C$ NMR (DMSO-$d_6$, 400 MHz) δ 155.3, 153.6, 151.6, 147.6, 139.1, 129.5, 127.9 (2×), 119.2, 114.4 (2×), 87.6, 85.6, 73.3, 70.5, 61.5, 42.4; ESI-HRMS calcd for $C_{17}H_{20}N_5O_5$: 374.1459. found: m/z 374.1412 [M+H]$^+$.

N[6]-(3-Indolylethyl)adenosine (6)

In a round-bottomed flask (10 mL) were placed a solution of 6-chloropurine ribonucleoside (71 mg, 0.25 mmol), trypamine (101 mg, 0.63 mmol) and diisopropylethylamine (0.24 mL, 2.88 mmol) in EtOH (3 mL). The flask was placed into the cavity of a focused monomode microwave reactor, and irradiated at 150 W for 10 min in refluxing EtOH. The mixture was concentrated by rotary evaporation, and the residue was purified by flash chromatography (silica gel; MeOH/EtOAc (1:9)) to give the title compound 6 (85 mg, 83%). The purity of product was >99% as shown by HPLC on an HC-C18 column (Agilent, 4.6×250 mm, 5 μm) with elution of gradients of 30-60% aqueous $CH_3CN$. $C_{20}H_{22}N_6O_4$; white powder; mp 187.0-187.2° C.; $[\alpha]^{20}_D=-55.7$ ($CH_3OH$, c=1.0); TLC (MeOH/EtOAc (1:9)) $R_f=0.41$; $^1H$ NMR (DMSO-$d_6$, 400 MHz) δ 10.78 (1H, s), 8.33 (1H, s), 8.25 (1H, s), 7.96 (1H, br s), 7.61 (1H, d, J=7.2 Hz), 7.32 (1H, d, J=9.2 Hz), 7.18 (1H, s), 7.05 (1H, t, J=8.0 Hz), 5.80 (1H, d, J=6.0 Hz), 5.47-5.44 (2H, m), 5.20 (1H, d, J=4.4 Hz), 4.61 (1H, d, J=5.6 Hz), 4.14 (1H, d, J=2.8 Hz), 3.96 (1H, d, J=3.2 Hz), 3.77 (1H, br s), 3.69-3.52 (2H, m), 3.01 (2H, t, J=7.2 Hz); $^{13}C$ NMR (DMSO-$d_6$, 100 MHz) δ 154.3, 152.2, 148.0, 139.5, 136.0, 127.1, 122.4, 120.8, 119.6, 118.3, 118.1, 111.7, 111.2, 87.9, 85.8, 73.4, 70.6, 61.6, 40.5, 25.1; ESI-HRMS calcd for $C_{20}H_{23}N_5O_4$: 411.1775. found: m/z 411.1750 [M+H]$^+$.

5'-Azido-5'-deoxy-2',3'-O-isopropylidene-N[6]-(4-methoxybenzyl)adenosine (8-actonide)

To the acetonide of N[6]-(4-methoxybenzyl) adenosine (3-acetonide, 2.96 g, 6.9 mmol) in anhydrous pyridine (36 mL) was added a solution of p-toluenesulfonyl chloride (6.3 g, 34.6 mmol) in anhydrous pyridine (6.0 mL) dropwise via syringe to a solution of. The mixture was stirred at room temperature for 6 h. Pyridine was removed under reduced pressure, and the residue was extracted with $CH_2Cl_2$ and $H_2O$. The organic layer was dried over $MgSO_4$, filtered, and concentrated to give a mixture of sulfonate and the chloride derivatives (5:1) as shown by the $^1H$ NMR spectrum.

The above-prepared mixture was dissolved in anhydrous DMF (70 mL), and sodium azide (1.34 g, 20.6 mmol) was added. The mixture was stirred at 80° C. for 6 h, and then concentrated under reduced pressure. The residue was extracted with $CH_2Cl_2$ and $H_2O$. The organic layer was dried over $MgSO_4$, filtered, and concentrated to give a pale yellow oil, which was purified by flash chromatography (silica gel; $CH_2Cl_2$/MeOH (100:1)) to give 8-acetonide (653 mg, 21% overall yield). $C_{21}H_{24}N_8O_4$; colorless oil; TLC (EtOAc/Hexane (6:4)) $R_f=0.39$; $[\alpha]^{23}_D=+5.0$ (EtOAc, c=1.0); IR $v_{max}$ (neat) 3280, 2987, 2931, 2101, 1618, 1512, 1478, 1375, 1330, 1296, 1218, 1211, 1154, 1091 cm$^{-1}$; $^1H$ NMR (CDCl$_3$, 400 MHz) δ 8.38 (1H, br s), 7.72 (1H, br s), 7.26 (2H, d, J=8.8 Hz), 6.84 (2H, d, J=8.8 Hz), 6.37 (1H, br s), 6.06 (1H, d, J=2.0 Hz), 5.46-5.44 (1H, m), 5.07-5.05 (1H, m), 4.77 (2H, br s), 4.38-4.35 (1H, m), 3.77 (3H, s), 3.51-3.62 (2H, m), 1.61 (3H, s), 1.39 (3H, s); $^{13}C$ NMR (CDCl$_3$, 100 MHz) δ 158.7, 154.5, 153.1, 147.9, 139.0, 130.2, 128.8 (2×), 120.1, 114.4, 113.8 (2×), 90.4, 85.6, 83.9, 82.0, 55.2, 52.2, 43.7, 29.7, 27.1, 25.3; ESI-HRMS calcd for $C_{21}H_{24}N_8O_4$: 453.1999. found: m/z 453.1999 $[M+H]^+$.

5'-Acetamido-5'-deoxy-$N^6$-(4-methoxybenzyl)adenosine (9)

The azido compound 8-acetonide (95 mg, 0.21 mmol) was stirred with triphenylphosphine (66 mg, 0.24 mmol) in $THF/H_2O$ (10:1, 2 mL) at room temperature for 4.5 h. The mixture was concentrated under reduced pressure. The residue was taken up with $CH_2Cl_2$ and $H_2O$, and acidified with HCl solution (1 M) until pH=2. The aqueous phase was separated, neutralized with saturated $NaHCO_3$ aqueous solution, and extracted with $CH_2Cl_2$. The organic extract was dried over $MgSO_4$, filtered, and concentrated to yield a crude amine product.

The crude amine was treated with acetic anhydride (98.6 µL, 1.05 mmol) in anhydrous pyridine (0.2 mL). The mixture was stirred at room temperature for 1.5 h, and then concentrated under reduced pressure. The residue was extracted with $CH_2Cl_2$ and $H_2O$. The organic layer was dried over $MgSO_4$, filtered, concentrated, and purified by flash chromatography (silica gel; $CH_2Cl_2$/MeOH (98:2)) to give the acetonide of compound 9 (56 mg, 57% yield for 2 steps). The purity of product was >99% as shown by HPLC on an HC-C18 column (Agilent, 4.6×250 mm, 5 in) with elution of gradients of 30-60% aqueous $CH_3CN$. $C_{23}H_{28}N_6O_5$; colorless oil; TLC ($CH_2Cl_2$/MeOH (98:2)) $R_f$=0.2; $[\alpha]^{28}_D=-146.6$ ($CHCl_3$, c=1.0); IR $\nu_{max}$ (neat) 3280, 3062, 2989, 2930, 2835, 2358, 1667, 1620, 1513, 1376, 1336, 1296, 1246, 1215, 1096, 1034 $cm^{-1}$; $^1H$ NMR ($CDCl_3$, 400 MHz) δ 8.36-8.38 (2H, m), 7.73 (1H, s), 7.28 (2H, d, J=8.8 Hz), 6.86 (2H, d, J=8.8 Hz), 6.15 (1H, br s), 5.77 (1H, d, J=4.8 Hz), 5.26 (1H, t, J=4.8 Hz), 4.81 (1H, dd, J=4.0, 2.4 Hz), 4.76 (2H, br s), 4.47-4.48 (1H, m), 4.11-4.17 (1H, m), 3.79 (3H, s), 3.24 (1H, d, J=14.4 Hz), 2.15 (3H, s), 1.61 (3H, s), 1.34 (3H, s); $^{13}C$ NMR ($CDCl_3$, 100 MHz) δ 170.5, 158.8, 154.8, 152.7, 147.7, 139.7, 130.0, 128.9 (2×), 121.1, 114.6, 113.9 (2×), 92.5, 83.3, 82.2, 81.3, 55.3, 43.9, 41.1, 27.6, 25.4, 23.2; ESI-HRMS calcd. for $C_{23}H_{28}N_6O_5$: 469.2190. found m/z 469.2193 $[M+H]^+$.

The acetonide of 9 (17.2 mg, 0.037 mmol) was stirred in 3 M HCl/THF (1:1, 0.1 mL) at room temperature for 14 h, and then neutralized with saturated $NaHCO_3$ aqueous solution. The mixture was concentrated under reduced pressure, and the residue was extracted with $CH_2Cl_2$ and $H_2O$. The organic layer was dried over $MgSO_4$, filtered, and concentrated to give the title compound 9 (11 mg, 70%). The purity of product 9 was 99% as shown by HPLC on an HC-C18 column (Agilent, 4.6×250 mm, 5 µm) with elution of gradients of 30-60% aqueous $CH_3CN$ in 20 min. $C_{20}H_{24}N_6O_5$; white powder; mp 121.1-121.6° C.; TLC ($CH_2Cl_2$/MeOH (9:1)) $R_f$=0.5; $[\alpha]^{25}_D=-108.7$ (THF, c=0.89); IR $\nu_{max}$ (neat) 3275, 3071, 2923, 2852, 2360, 1621, 1512, 1375, 1339, 1297, 1245, 1175, 1126, 1076 $cm^{-1}$; $^1H$ NMR ($CDCl_3$, 400 MHz) δ 8.76 (1H, s), 8.27 (1H, s), 7.24 (2H, d, J=8.4 Hz), 6.81 (2H, d, J=8.4 Hz), 6.54 (1H, s), 5.70 (1H, d, J=5.6 Hz), 4.72 (3H, d, J=5.6 Hz), 4.23 (1H, s), 4.18 (1H, s), 3.98-4.03 (1H, m), 3.75 (3H, s), 3.13 (1H, d, J=14.0 Hz), 2.02 (3H, s); $^{13}C$ NMR (DMSO, 100 MHz) δ 169.4, 157.9, 154.3, 152.3, 148.3, 140.2, 131.8, 128.4 (2×), 119.8, 113.5 (2×), 87.9, 83.6, 72.6, 71.3, 55.1, 42.4, 41.1, 22.7; ESI-HRMS calcd for $C_{26}H_{24}N_6O_5$: 427.1730. found: m/z 427.1727 $[M+H]^+$.

5'-Deoxy-5'-(4-methyl-1,2,3-triazol-1-yl)-$N^6$-(4-methoxybenzyl)adenosine (11)

A mixture of azido compound 8-acetonide (313 mg, 0.69 mmol), $CuSO_4 \cdot 5H_2O$ (24.9 mg), sodium ascorbate (61.4 mg) and propargyl alcohol in $H_2O$/t-BuOH (1:1, 7 mL) was stirred at room temperature for 12 h, and then concentrated under reduced pressure. The residue was extracted with $CH_2Cl_2$ and $H_2O$. The organic layer was dried over $MgSO_4$, filtered, and concentrated to yield a triazole acetonide (~220 mg) as colorless oil. TLC ($CH_2Cl_2$/MeOH (9:1)) $R_f$=0.5; ESI-HRMS calcd for $C_{24}H_{26}N_8O_5$: 509.2261. found: m/z 509.2267 $[M+H]^+$.

The above-prepared triazole compound was stirred with triethylamine (0.15 mL, 1.08 mmol) and methylsulfonyl chloride (0.08 mL, 1.08 mmol) in anhydrous $CH_2Cl_2$ (4.3 mL) at room temperature for 2 h. The mixture was concentrated under reduced pressure, and the residue was extracted with $CH_2Cl_2$ and $H_2O$. The organic layer was dried over $MgSO_4$, filtered, and concentrated to yield a mesylate compound as colorless oil. TLC (EtOAc/Hex (4:1)) $R_f$=0.45; ESI-HRMS calcd for $C_{25}H_{30}N_6O_7SNa$: 609.1856. found: m/z 609.1876 $[M+Na]^+$.

The mesylate was treated with $NaBH_4$ (24.5 mg, 0.65 mmol) at 0° C. in DMF, and then heated to 60° C. for 6 h. The mixture was concentrated under reduced pressure, and the residue was extracted with $CH_2Cl_2$ and $H_2O$. The organic layer was dried over $MgSO_4$, filtered, and concentrated to give 11-acetonide as colorless oil. TLC (EtOAc/Hex (4:1)) $R_f$=0.25; ESI-HRMS calcd for $C_{24}H_{28}N_8O_4$: 493.2312. found: m/z 493.2312 $[M+H]^+$.

The acetonide of 11 was stirred in 3 M HCl/THF (1:1, 0.33 mL) at room temperature for 14 h, and then neutralized with saturated $NaHCO_3$ aqueous solution. The mixture was concentrated under reduced pressure, and the residue was dissolved in THF, filtered, and concentrated to give the title compound 11 (48.1 mg, 25% overall yield). The purity of product was 98% as shown by HPLC on an HC-C18 column (Agilent, 4.6×250 mm, 5 µm) with elution of gradients of 30-60% aqueous $CH_3CN$. $C_{21}H_{24}N_6O_4$; white powder; mp 183.0-183.2° C.; TLC ($CH_2Cl_2$/MeOH (9:1)) $R_f$=0.12; $[\alpha]^{27}_D$+20.3 ($CH_3OH$, c=0.45); IR $\nu_{max}$ (neat) 3217, 2921, 2850, 2685, 1620, 1513, 1470, 1337, 1297, 1244, 1176, 1111, 1058 $cm^{-1}$; $^1H$ NMR ($CD_3OD$, 400 MHz) δ 8.22 (1H, s), 7.99 (1H, s), 7.45 (1H, s), 7.31 (2H, d, J=8.8 Hz), 6.87 (2H, d, J=8.8 Hz), 5.96 (1H, d, J=4.0 Hz), 4.82-4.68 (5H, m), 4.46 (1H, t, J=4.0 Hz), 4.34 (1H, q, J=4.0 Hz), 3.77 (3H, s), 2.15 (3H, s); $^{13}C$ NMR ($CDCl_3$, 100 MHz) δ 158.7, 154.2, 152.9, 148.0, 142.8, 138.8, 130.1, 128.8 (2×), 123.1, 119.6, 113.8 (2×), 89.3, 82.2, 73.4, 70.8, 55.2, 50.9, 43.9, 10.5; ESI-HRMS (negative mode) calcd for $C_{21}H_{24}N_8O_4$: 451.1842. found: m/z 451.1843 $[M-H]^-$.

3,4-Dihydroxy-5-[6-(4-hydroxybenzylamino)-purin-9-yl]-tetrahydrofuran-2-carboxylic Acid Ethylamide (15)

The acetonide derived from 6-chloropurine ribofuranoside (17-acetonide, 158 mg, 0.48 mmol) was stirred with $PhI(OAc)_2$ (509 mg, 1.56 mmol) and 2,2,6,6-tetramethylpiperidinyl-1-oxy (TEMPO, 15.4 mg, 0.1 mmol) in a degassed $CH_3CN/H_2O$ solution (1:1, 2.6 mL) at 40° C. for 4 h. The mixture was concentrated under reduced pressure to yield a crude acid product 18.

The crude acid was treated with ethylamine (117 mg, as the hydrochloric salt), O-(benzotriazol-1-yl)-N,N,N',N'-tetramethyluronium hexafluorophosphate (HBTU, 375 mg, 0.72 mmol) and diisopropylethylamine (0.5 ml, 2.89 mmol) in anhydrous DMF (11.6 mL) at room temperature for 14 h. The mixture was concentrated under reduced pressure. The residue was extracted with $CH_2Cl_2$ and $H_2O$. The organic layer was dried over $MgSO_4$, filtered, concentrated, and purified by flash chromatography (silica gel; EtOAc/hexane (1:1)) to yield an amide product 19 as colorless oil. The amide product was treated with 4-hydroxybenzylamine (385 mg, 2.4 mmol as the hydrochloric salt) and diisopropylethylamine (2.8 mL, 16.9 mmol) in 1-propanol (28 mL) at 70° C. for 2 h. The mixture was concentrated under reduced pressure, and the residue was extracted with $CH_2Cl_2$ and $H_2O$. The organic layer was dried over $MgSO_4$, filtered, concentrated, and purified by flash chromatography (silica gel; $CH_2Cl_2$/MeOH (97:3)) to give 15-acetonide (179 mg, 82%). $C_{23}H_{23}N_6O_5$; colorless oil; TLC (EtOAc/hexane (4:1)) $R_f$=0.13; $[\alpha]^{22}_D$=−32.0 (EtOAc, c=1.0); IR $\nu_{max}$ (neat) 3347, 3103, 2982, 2933, 1732, 1667, 1615, 1516, 1479, 1461, 1376, 1332, 1295, 1245, 1212, 1154, 1088 cm$^{-1}$; $^1$H NMR (CDCl$_3$, 400 MHz) δ 9.01 (1H, br s), 8.35 (1H, br s), 7.81 (1H, s), 7.14 (1H, br s), 7.04 (2H, d, J=8.0 Hz), 6.68 (2H, d, J=8.0 Hz), 6.49 (1H, t, 4.8 Hz), 6.03 (1H, d, J=2.4 Hz), 5.33-5.38 (2H, m), 4.70 (3H, s), 3.09-3.16 (2H, m), 1.62 (3H, s), 1.37 (3H, s), 0.90 (3H, t, J=7.2 Hz); $^{13}$C NMR (CDCl$_3$, 100 MHz) δ 168.7, 155.8, 154.2, 153.1, 147.7, 139.1, 128.8 (3×), 119.6, 115.4 (2×), 114.3, 91.6, 85.6, 83.3, 82.4, 43.9, 34.0, 27.0, 25.1, 14.2; ESI-HRMS calcd for $C_{22}H_{26}N_6O_5$: 455.2043. found: m/z 455.2037 [M+H]$^+$.

The acetonide of 15 (26 mg, 0.057 mmol) was stirred in 1 M HCl/THF (1:1, 0.3 mL) at room temperature for 16 h, and then neutralized with saturated NaHCO$_3$ aqueous solution. After concentration, the residue was triturated with $H_2O$ to give the title compound 15, which was then recrystallized from MeOH (14.65 mg, 62%). $C_{19}H_{22}N_6O_5$; white powder; mp 179.7-180.5° C.; TLC (EtOAc) $R_f$=0.04; $[\alpha]^{23}_D$=−27.7 (MeOH, c=1.0); IR $\nu_{max}$ (neat) 3256, 2688, 2360, 1618, 1515, 1335, 1294, 1232, 1128, 1052 cm$^{-1}$; $^1$H NMR (CD$_3$OD, 400 MHz) δ 8.29 (1H, s), 8.22 (1H, s), 7.20 (2H, d, J=8.4 Hz), 6.73 (2H, d, J=8.4 Hz), 6.00 (1H, d, J=7.6 Hz), 4.76-4.73 (1H, m), 4.70 (2H, br s), 4.46 (1H, s), 4.30-4.31 (1H, m), 3.36 (2H, q, 7.2 Hz), 1.21 (3H, t, 7.2 Hz); $^{13}$C NMR (CD$_3$OD, 100 MHz) δ 171.8, 157.5, 155.8, 153.6, 149.1, 141.9, 130.5, 129.9 (2×), 121.3, 116.2 (2×), 90.5, 86.3, 74.9, 73.4, 44.9, 35.2, 15.3; ESI-HRMS calcd for $CF_{19}H_{21}N_6O_5$: 413.1573. found: m/z 413.1573 [M−H]$^+$. Anal. Calcd for $C_{19}H_{22}N_6O_5 \cdot H_2O$: C, 52.77; H, 5.59; N, 19.43. found: C, 52.88; H, 5.40; N, 19.44.

2-[6-(4-Methoxybenzylamino)-purin-9-yl]-5-(1H-tetrazol-5-yl)-tetrahydrofuran-3,4-diol (16)

The crude acid 18 obtained from oxidation of 17-acetonide (ca. 3.98 mmol) with PhI(OAc)$_2$/TEMPO was treated with ammonium chloride (426 mg, 7.96 mmol), benzotriazol-1-yl-oxytripyrrolidinophosphonium hexafluorophosphate (PyBOP, 3.07 g, 5.97 mmol), hydroxybenzotriazole (HOBt, 807 mg, 5.97 mmol) and diisopropylethylamine (2.5 mL, 15.9 mmol) in anhydrous DMF (40 mL) at 50° C. for 14 h. The mixture was concentrated under reduced pressure. The residue was extracted with $CH_2Cl_2$ and $H_2O$. The organic layer was dried over $MgSO_4$, filtered, concentrated, and purified by flash chromatography (silica gel; EtOAc/hexane (1:1 to 4:1)) to yield an amide product 20 as colorless oil.

A solution of dimethyl sulfoxide (0.85 mL, 11.9 mmol) in $CH_2Cl_2$ (10 mL) was added to a solution of oxalyl chloride (0.7 mL, 7.96 mmol) in $CH_2Cl_2$ (10 mL) at −78° C. The mixture was stirred for 30 min, and a solution of amide 20 (ca. 3.98 mmol) in $CH_2Cl_2$ (20 mL) was added. The mixture was stirred at −78° C. for another 30 min, and diisopropylethylamine (2.6 mL, 15.9 mmol) was added. After 1 h stirring, formation of nitrile 21 was monitored by TLC analysis. The mixture was extracted with $CH_2Cl_2$ and $H_2O$. The organic phase was dried over $MgSO_4$, filtered, concentrated, and purified by flash chromatography (silica gel; EtOAc/hexane (2:3)) to yield nitrile 21 as colorless oil (863 mg) contaminated with a small amount of HOBt.

The above-prepared nitrile product (863 mg, 2.68 mmol) was treated with 4-methoxybenzylamine (1.84 g, 13.4 mmol) and diisopropylethylamine (15.5 mL) in 1-propanol (26 mL) at 70° C. for 4 h. The mixture was concentrated under reduced pressure, and the residue was extracted with $CH_2Cl_2$ and $H_2O$. The organic layer was dried over $MgSO_4$, filtered, concentrated, and purified by flash chromatography (silica gel; $CH_2Cl_2$/MeOH (300:1 to 150:1)) to give compound 22 (905 mg, 54% overall yield). $C_{21}H_{22}NO_4$; colorless oil; TLC (EtOAc/hexane (4:1)) $R_f$=0.55; $[\alpha]^{26}_D$=+25.8 (EtOAc, c=1.0); IR $\nu_{max}$ (neat) 3373, 3282, 2990, 2925, 2853, 1679, 1618, 1.512, 1465, 1376, 1331, 1295, 1249, 1212, 1135, 1086 cm$^{-1}$; $^1$H NMR (CDCl$_3$, 400 MHz) δ 8.39 (1H, br s), 7.64 (1H, br s), 7.26 (2H, d, J=10.4 Hz), 6.83 (2H, d, J=10.4 Hz), 6.54 (1H, t, J=5.6 Hz), 6.13 (1H, s), 5.77 (1H, d, J=4.0 Hz), 5.68 (1H, dd, J=1.6, 4.0 Hz), 4.95 (1H, d, J=1.6 Hz), 4.75 (2H, br s), 3.79 (3H, s), 1.57 (3H, s), 1.42 (3H, s); $^{13}$C NMR (CDCl$_3$, 100 MHz) δ 158.8, 154.5, 153.2, 148.2, 138.9, 130.2, 128.9 (2×), 119.7, 115.9, 114.5, 113.9 (2×), 91.6, 84.6, 83.9, 75.1, 55.3, 44.0, 26.6, 25.1; ESI-HRMS (negative mode) calcd for $C_{21}H_{22}N_6O_4$: 421.1624. found: m/z 421.1612 [M−H]$^-$.

A solution of nitrile 22 (905 mg, 2.14 mmol) and NH$_4$Cl (429 mg, 8.04 mmol) in DMF (20 mL) was cooled to 0° C., and added NaN$_3$ (523 mg, 8.04 mmol). The ice bath was removed; the mixture was heated to 40° C. for 1 h, slowly to 90° C., and kept stirring at 90° C. for 9 h. The mixture was cooled, concentrated under reduced pressure, dissolved in EtOAc, and extracted with NaHCO$_3$ aqueous solution (pH=8). The combined aqueous phase was acidified by addition of HCl solution (1 M) until pH=2, and extracted with $CH_2Cl_2$. The organic layer was dried over $MgSO_4$, filtered, and concentrated to give a practically pure tetrazole product 16-acetonide as colorless oil (460 mg, 46% yield). $C_{23}H_{23}N_3O_4$; TLC ($CH_2Cl_2$/MeOH (9:1)) $R_f$=0.25; $[\alpha]^{27}_D$=13.2 (EtOAc, c=1.0); IR $\nu_{max}$ (neat) 3361, 2926, 2852, 1613, 1513, 1481, 1375, 1333, 1293, 1249, 1210, 1176, 1154, 1101, 1034 cm$^{-1}$; $^1$H NMR (CDCl$_3$, 400 MHz) δ 7.90 (1H, br s), 7.68 (1H, br s), 7.35 (2H, d, J=8.4 Hz), 6.86 (2H, d, J=8.4 Hz), 6.83 (1H, br s), 6.18 (1H, s), 5.85 (1H, s), 5.73 (1H, d, J=6.0 Hz), 5.49 (1H, d, J=6.0 Hz), 4.92 (1H, dd, J=6.8, 7.6 Hz), 4.39 (1H, dd, J=4.0, 10.4 Hz), 3.77 (3H, s), 1.69 (3H, s), 1.43 (3H, s); $^{13}$C NMR (CDCl$_3$, 100 MHz) δ 158.4, 154.9, 152.9, 152.6, 146.2, 138.5, 129.5, 129.2 (2×), 118.4, 114.2, 113.7 (2×), 93.4, 85.9, 83.7, 82.3, 55.4, 44.1, 27.1, 25.2; ESI-HRMS (negative mode) calcd for $C_{21}H_{23}N_9O_4$: 464.1795. found: m/z 1786 [M−H]$^-$.

Compound 16-acetonide (460 mg, 0.99 mmol) was stirred in 3 M HCl/THF (1:1, 0.1 mL) at room temperature for 14 h, and then neutralized with saturated NaHCO$_3$ aqueous solution. The mixture was concentrated under reduced pressure; the residue was taken up with THF, filtered, and concentrated to give the title compound 16 (320 mg, 76%). The purity of product was 99% as shown by HPLC on an HC-C18 column (Agilent, 4.6×250 mm, 5 μm) with elution of gradients of 30-60% aqueous $CH_3CN$ in 20 min. $C_{18}H_{19}N_9O_4$; white powder; mp 210.0-210.6° C.; TLC ($CH_2Cl_2$/MeOH (9:1)) $R_f$=0.05; $[\alpha]^{26}_D$=−25.8 (THF, c=1.0); IR $\nu_{max}$ (neat) 3397, 2841, 2692, 1623, 1511, 1475, 1419, 1339, 1302, 1236, 1180, 1124, 1045 cm$^{-1}$; $^1$H NMR (DMSO-d$_6$, 400 MHz) δ 8.82 (1H, s), 8.30 (1H, br s), 8.20 (1H, s), 7.26 (2H, d, J=8.0 Hz), 6.83 (2H, d, J=8.0 Hz), 6.08

(1H, d, J=5.6 Hz), 5.53 (1H, d, J=6.0 Hz), 5.46 (1H, d, J=2.8 Hz), 5.18 (1H, s), 4.91 (1H, d, J=5.2 Hz), 4.62 (2H, br s), 4.20 (1H, s), 3.69 (3H, d, J=2.0 Hz); $^{13}$C NMR (DMSO-$d_6$, 100 MHz) δ 159.9, 157.4, 153.7, 151.9, 138.8, 131.5, 127.9 (2×), 113.1 (2×), 85.9, 79.1, 75.4, 74.3, 54.6, 41.9; ESI-HRMS (negative mode) calcd for $C_{18}H_{19}N_9O_4$: 427.1730. found: m/z 427.1727 [M−H]$^-$.

Radioligand Binding Assays.

Radioligand binding assays were performed by MDS Pharma Services Taiwan (Taipei, Taiwan) using standard binding protocols. For the binding assay of the $A_{2A}$ receptor,[46] membrane proteins collected from HEK293 cells overexpressing the human $A_{2A}$ receptor were incubated in reaction buffer [50 mM Tris-HCl (pH 7.4), 10 mM $MgCl_2$, 1 mM EDTA, and 2 U/mL adenosine deaminase] containing $^3$H-CGS21680 (50 nM) for 90 min at 25° C. Nonspecific binding was assessed in the presence of 50 µM adenosine-5'-N-ethylcarboxamide (NECA).

Binding assays for adenosine transporters were conducted as described earlier.[47] Membrane fractions collected from the cerebral cortex of Duncan Hartley derived guinea pigs were incubated with $^3$H-labeled NBTI (0.5 nM) for 30 min at 25° C. in an incubation buffer containing 50 mM Tris-HCl (pH 7.4). Nonspecific binding was assessed in the presence of 5 µM NBTI, a high-affinity inhibitor of equilibrative nucleoside transporter 1 (ENT1), which inhibits only ENT1 at 0.5 nM.[48] Reactions were terminated by filtration over GF/B glass fibers and washing with the corresponding reaction buffer.

MTT Metabolism Assay.

PC12 cells purchased from ATCC (Manassas, Va., USA) were maintained in Dulbecco's modified Eagle's medium (DMEM) supplemented with 10% horse serum and 5% fetal bovine serum and incubated in a $CO_2$ incubator (5%) at 37° C. Survival was assessed by the 3-(4,5-dimethylthiazol-2-yl)-2,5-diphenyltetrazolium bromide (MTT) metabolism assay as described elsewhere.[49,50] In brief, cells grown on 150-mm plates were washed three times with PBS and resuspended in DMEM. Suspended cells (1×10$^4$ cells) were plated on 96-well plates and treated with or without the indicated reagent. After incubation for 24 h, MTT (0.5 mg/mL) was added to the medium and incubated for 3 h. After discarding the medium, DMSO (100 µL) was then applied to the well to dissolve the formazan crystals derived from the mitochondrial cleavage of the tetrazolium ring by live cells. The absorbance at 570/630 nm in each well was measured on a micro-enzyme-linked immunosorbent assay (ELISA) reader.

CITATION LIST

1. Andrew, S. E.; Goldberg, Y. P.; Kremez, B.; Telenius, H.; Theilmann, J.; Adam, S.; Starr, E.; Squitieri, F.; Lin, B.; Kalchman, M. A.; Graham, R. K.; Hayden, M. R. The relationship between trinucleotide (CAG) repeat length and clinical features of Huntington's disease. *Nat. Genet.* 1993, 4, 398-403.
2. DiFiglia, M.; Sapp, E.; Chase, K. O.; Davies, S. W.; Bates, G. P.; Vonsattel, J. P.; Aronin, N. Aggregation of huntingtin in neuronal intranuclear inclusions and dystrophic neurites in brain. *Science* 1997, 277, 1990-1993.
3. MacDonald, M. E.; Ambrose, C. M.; Duyao, M. P.; Myers, R. H.; Lin, C.; Srinidhi, L.; Barnes, G.; Taylor, S. A.; James, M.; Groot, N. A novel gene containing a trinucleotide repeat that is expanded and unstable on Huntington's disease chromosomes. *Cell* 1993, 72, 971-983.
4. Beal, M. F.; Ferrante, R. J. Experimental therapeutics in transgenic mouse models of Huntington's disease. *Nat. Rev. Neurosci.* 2004, 5, 373-384.
5. Okamoto, S.-i.; Pouladi, M. A.; Talantova, M.; Yao, D.; Xia, P.; Dagmar Ehrnhoefer. E.; Zaidi, R.; Clemente, A.; Kaul, M.; Graham, R. K.; Zhang, D.; Chen, H.-S. V.; Tong, G.; Hayden, M. P.; Lipton, S. A. Balance between synaptic versus extrasynaptic NMDA receptor activity influences inclusions and neurotoxicity of mutant huntingtin. *Nat. Med.* 2009, 15, 1407-1413.
6. Chou, S. Y.; Lee, Y. C.; Chen, H. M.; Chiang, M. C.; Lai, H. L.; Chang, H. H.; Wu, Y. C.; Sun, C. N.; Chien, C. L.; Lin, Y. S.; Wang, S. C.; Tung, Y. Y.; Chang, C.; Chern, Y. CGS21680 attenuates symptoms of Huntington's disease in a transgenic mouse model. *J. Neurochem.* 2005, 93, 310-320.
7. Chiang, M. C.; Chen, H. M.; Lai, H. L.; Chen, H. W.; Chou, S. Y.; Chen, C. M.; Tsai, F. J.; Chern, Y. The $A_{2A}$ adenosine receptor rescues the urea cycle deficiency of Huntington's disease by enhancing the activity of the ubiquitin-proteasome system. *Hum. Mol. Genet.* 2009, 18, 2929-2942.
8. Link, A. A.; Kino, T.; Worth, J. A.; McGuire, J. L.; Crane, M. L.; Chrousos, G. P.; Wilder, R. L.; Elenkov, I. J. Ligand-activation of the adenosine $A_{2A}$ receptors inhibits IL-12 production by human monocytes. *J. Immunol.* 2000, 164, 436-442.
9. Huang, N.-K.; Chern, Y.; Fang, J.-M.; Lin, C.-I; Chen, W.-P.; Lin, Y.-L. Neuroprotective principles from *Gastrodia elata*. *J. Nat. Prod.* 2007, 70, 571-574.
10. Fink, J. S.; Weaver, D. R; Rivkees, S. A; Peterfreund, R. A.; Pollack, A. E.; Adler, E. M.; Reppert, S. M. Molecular cloning of the rat $A_2$ adenosine receptor: selective co-expression with $D_2$ dopamine receptors in rat striatum. *Brain Res. Mol. Brain Res.* 1992, 14, 186-195.
11. Dixon, A. K.; Gubitz, A. K.; Sizinathsinghji, D. J. S.; Richardson, P. J.; Freeman, T. C. Tissue distribution of adenosine receptor mRNAs in the rat. *Br. J. Pharmacol.* 1996, 118, 1461-1468.
12. Rosin, D. L.; Robeva, A.; Woodard, R. L.; Guyenet, P. G.; Linden, J. Immunohistochemical localization of adenosine $A_{2A}$ receptors in the rat central, nervous system. *J. Comp. Neurol.* 1998, 401, 163-186.
13. Anderson, C. M.; Xiong, H.; Geiger, J. D.; Young, J. D.; Cass, C. E.; Baldwin, S. A.; Parkinson, F. E. Distribution of equilibrative, nitrobenzylthioinosine-sensitive nucleoside transporters (ENT1) in brain. *J. Neurochem.* 1999, 73, 867-873.
14. Sapp, E.; Schwarz, C.; Chase, K.; Bhide, P. G.; Young, A. B.; Penney, J.; Vonsattel, J. P.; Aronin, N.; DiFiglia, M. Huntingtin localization in brains of normal and Huntington's disease patients. *Ann. Neurol.* 1997, 42, 604-612.
15. Ohlson, S. Designing transient binding drugs: A new concept for drug discovery. *Drug Discov. Today* 2008, 13, 433-439.
16. Morphy, R.; Kay, C.; Rankovic, Z. From magic bullets to designed multiple ligands. *Drug Discov. Today* 2004, 9, 641-651.
17. Morphy, R.; Rankovic, Z. Designed multiple ligands. an emerging drug discovery paradigm. *J. Med. Chem.* 2005, 48, 6523-6543.
18. Zimmermann, G. R.; Lehar, J.; Keith, C. T. Multi-target therapeutics: when the whole is greater than the sum of the parts. *Drug Discov. Today* 2007, 12, 34-42.
19. Hopkins, A. L. Network pharmacology: the next paradigm in drug discovery. *Nat. Chem. Bio.* 2008, 4, 682-690.

20. Popoli, P.; Blum, D.; Domenici, M. R.; Burnouf, S.; Chern, Y. A critical evaluation of adenosine $A_{2A}$ receptors as potentially "druggable" targets in Huntington's disease. *Curr. Pharm. Des.* 2008, 14, 1500-1511.
21. Morphy, R.; Rankovic, Z. The Physicochemical challenges of designing multiple ligands. *J. Med. Chem.* 2006, 49, 4961-4970.
22. Morphy, R.; Rankovic, Z. Designing multiple ligands—medicinal chemistry strategies and challenges. *Curr. Pharm. Des.* 2009, 15, 587-600.
23. Kurogi, Y.; Güner, O. Pharmacophore modeling and three-dimensional database searching for drug design using catalyst. *Curr. Med. Chem.* 2001, 8, 1035-1055.
24. Kaminski, J. J.; Rane, D. F.; Snow, M. E.; Weber, L.; Rothofsky, M. L.; Anderson, S. D.; Lin, S. L. Identification of novel farnesyl protein transferase inhibitors using three-dimensional database searching methods. *J. Med. Chem.* 1997, 40, 4103-4112.
25. Singh, J.; Van Vlijmen, H.; Liao, Y.; Lee, W. C.; Cornebise, M.; Harris, M.; Shu, I. H.; Gill, A.; Cuervo, J. H.; Abraham, W. M.; Adams, S. P. Identification of potent and novel $\alpha 4\beta 1$ antagonists using in silico screening. *J. Med. Chem.* 2002, 45, 2988-2993.
26. Kotsikorou, E.; Oldfield, E. A quantitative structure-activity relationship and pharmacophore modeling investigation of aryl-X and heterocyclic bisphosphonates as bone resorption agents. *J. Med. Chem.* 2003, 46, 2932-2944.
27. Chen, G. S.; Chang, C. S.; Kan, W. M.; Chang, C. L.; Wang, K. C.; Chern, J. W. Novel lead generation through hypothetical pharmacophore three-dimensional database searching: discovery of isoflavonoids as nonsteroidal inhibitors of rat 5$\alpha$-reductase. *J. Med. Chem.* 2001, 44, 3759-3763.
28. Zampieri, D.; Mamolo, M. G.; Laurini, E.; Florio, C.; Zanette, C.; Fermeglia, M.; Posocco, P.; Paneni, M. S.; Pricl, S.; Vie, L. Synthesis, biological evaluation, and three-dimensional in silico pharmacophore model for $\sigma_1$ receptor ligands based on a series of substituted benzo[d]oxazol-2(3H)-one derivatives. *J. Med. Chem.* 2009, 52, 5380-5393.
29. Wei, D.; Jiang, X.; Zhou, L.; Chen, J.; Chen, Z.; He, C.; Yang, K.; Liu, Y.; Pei, J.; Lai, L. Discovery of multitarget inhibitors by combining molecular docking with common pharmacophore matching. *J. Med. Chem.* 2008, 51, 7882-7888.
30. Jaakola, V. P.; Griffith, M. T.; Hanson, M. A.; Cherezov, V.; Chien, E. Y.; Lane, J. R.; Ijzerman, A. P.; Stevens, R. C. The 2.6 angstrom crystal structure of a human $A_{2A}$ adenosine receptor bound to an antagonist. *Science* 2008, 322, 1211-1217.
31. Walkinshaw, G. & Waters, C. M. Neurotoxin-induced cell-death in neuronal pc2 cells is mediated by induction of apoptosis. *Neuroscience* 1994, 63, 975-987.
32. Chiang, M. C.; Lee, Y. C.; Huang, C. L.; Chern, Y. cAMP-response element-binding protein contributes to suppression of the $A_{2A}$ adenosine receptor promoter by mutant Huntingtin with expanded polyglutamine residues. *J. Biol. Chem.* 2005, 280, 14331-14340.
33. Jarvis, M. F.; Schulz, R.; Hutchison, A. J.; Do, U. H.; Sills, M. A.; Williams, M. ([$^3$H]CGS 21680, a selective $A_2$ adenosine receptor agonist directly labels $A_2$ receptors in rat brain. *J. Pharmacol. Exp. Ther.* 1989, 251, 888-893.
34. Catalyst, Accelrys, 9685 North Scranton Road, San Diego, Calif. 92121, U.S.A. http://www.accelrys.com
35. Cass, C. E.; Gaudette, L. A.; Paterson, A. R. Mediated transport of nucleosides in human erythrocytes—specific binding of inhibitor nitrobenzylthioinosine to nucleoside transport sites in erythrocyte-membrane. *Biochim. Biophys. Acta* 1974, 345, 1-10.
36. Zhu, Z. X.; Buolamwini, J. K. Constrained NBMPR analogue synthesis, pharmacophore mapping and 3D-QSAR modeling of equilibrative nucleoside transporter 1 (ENT1) inhibitory activity. *Bioorg. Med. Chem.* 2008, 16, 3848-3865.
37. Dixon, S. L.; Smondyrev, A. M.; Knoll, E. H.; Rao, S. N.; Shaw, D. E.; Friesner, R. A. PHASE: a new engine for pharmacophore perception, 3D QSAR model development, and 3D database screening: 1. Methodology and preliminary results. *J. Comput. Aided Mol. Des.* 2006, 20, 647-671.
38. Kolb, H. C.; Finn, M. G.; Sharpless, K. B. Click chemistry: diverse chemical function from a few good reactions. *Angew. Chem. Int. Ed.* 2001, 40, 2004-2021.
39. Epp, J. B.; Widlanski, T. S. Facile preparation of nucleoside-5'-carboxylic acids. *J. Org. Chem.* 1999, 64, 293-295.
40. Nakajima, N.; Saito, M.; Ubukata, M. Activated dimethyl sulfoxide dehydration of amide and its application to one-pot preparation of benzyl-type perfluoroimidates. *Tetrahedron*, 2002, 58, 3561-3577.
41. Bosch, M. P.; Campos, F.; Niubó, I.; Rosell, G.; Díaz, J. L.; Brea, J.; Loza, M. I.; Guerrero, A. Synthesis and biological activity of new potential agonists for human adenosine $A_{2A}$ receptor. *J. Med. Chem.* 2004, 47, 4041-4053.
42. Martin, P. L.; Barrett, R. J.; Linden, J.; Abraham, W. M. Pharmacology of 2-cyclohexylmethylidenehydrazinoadenosine (WRC-0470), a novel, short-acting adenosine $A_{2A}$ receptor agonist that produces selective coronary vasodilation. *Drug Develop. Res.* 1997, 40, 313-324.
43. Volpini, R.; Camaioni, E.; Costanzi, S.; Vittori, S.; Klotz, K. N.; Cristalli, G. Synthesis of di- and tri-substituted adenosine derivatives and their affinities at human adenosine receptor subtypes. *Nucleosides Nucleotides* 1999, 18, 2511-2520.
44. Vittori, S.; Costanzi, S.; Lambertucci, C.; Portino, F. P.; Taffi, S.; Volpini, R.; Klotz, K. N.; Cristalli, G. $A_{2B}$ adenosine receptor agonists: synthesis and biological evaluation of 2-phenylhydroxypropynyl adenosine and NECA derivatives. *Nucleosides, Nucleotides Nucleic Acids* 2004, 23, 471-481.
45. Güner, O.; Clement, O.; Kurogi, Y. Pharmacophore modeling and three dimensional database searching for drug design using catalyst: recent advances. *Curr. Med. Chem.* 2004, 11, 2991-3005.
46. Varani, K.; Gessi, S.; Dalpiaz, A.; Borea, P. A. Pharmacological and biochemical characterization of purified $A_{2A}$ adenosine receptors in human platelet membranes by [$^3$H]-CGS 21680 binding. *Br. J. Pharmacol.* 1996, 117, 1693-701.
47. Verma, A. & Marangos, P. J. Nitrobenzylthioinosine binding in brain: an interspecies study. *Life Sci.* 1985, 36, 283-290.
48. Ward, J. L.; Sherali, A.; Mo, Z. P.; Tse, C. M. Kinetic and pharmacological properties of cloned human equilibrative nucleoside transporters, ENT1 and ENT2, stably expressed in nucleoside transporter-deficient PK15 Cells. Ent2 exhibits a low affinity for guanosine and cytidine but a high affinity for inosine. *J. Biol. Chem.* 2000, 275, 8375-8381.
49. Mosmann, T. Rapid colorimetric assay for cellular growth and survival: application to proliferation and cytotoxicity assays. *J. Immunol. Methods.* 1983, 65, 55-63.
50. Huang, N. K.; Lin, Y. W.; Huang, C. L.; Messing, R. O.; Chern, Y. Activation of protein kinase A and a typical protein kinase C by $A_{2B}$ adenosine receptors antagonizes apoptosis due to serum deprivation in PC12 cells. *J. Biol. Chem.* 2001, 276, 13838-13846.

What is claimed is:

1. A method for treating neurodegenerative disease, comprising administering to a subject in need thereof an effective amount of a compound having the formula:

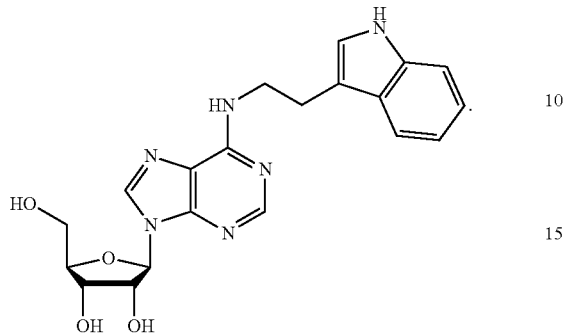

2. The method of claim 1, wherein the neurodegenerative disease is a protein-misfolding disease.

3. The method of claim 1, wherein the neurodegenerative disease is selected from the group consisting of Alzheimer's disease, Parkinson's disease, amyotrophic lateral sclerosis, Prion disease, Huntington's disease, and spinal cerebellar ataxias.

4. The method of claim 1, wherein the neurodegenerative disease is Huntington's disease.

* * * * *